United States Patent [19]
Lincoln, Jr. et al.

[11] 3,975,404
[45] Aug. 17, 1976

[54] BICYCLIC LACTONE INTERMEDIATES

[75] Inventors: Frank H. Lincoln, Jr., Portage; John E. Pike; Gilbert A. Youngdale, both of Kalamazoo, all of Mich.

[73] Assignee: The Upjohn Company, Kalamazoo, Mich.

[22] Filed: Feb. 20, 1975

[21] Appl. No.: 551,248

Related U.S. Application Data

[60] Continuation of Ser. No. 326,642, Jan. 26, 1973, abandoned, which is a division of Ser. No. 140,251, May 4, 1971, abandoned.

[52] U.S. Cl. .................................... 260/343.3 R
[51] Int. Cl.² ................................... C07D 307/77
[58] Field of Search ........................ 260/343.3

[56] References Cited
UNITED STATES PATENTS
3,778,450  12/1973  Axan ........................... 260/343.3

OTHER PUBLICATIONS

Corey et al. *Stereo–Controlled Synthesis of Prostaglandins* $F_{2r}$ *and* $E_2$(dl). J.A.C.S., 91, 9-24-69 pp. 5675–5677.

*Primary Examiner*—Henry R. Jiles
*Assistant Examiner*—C. M. S. Jaisle
*Attorney, Agent, or Firm*—Morris L. Nielsen

[57] ABSTRACT

Intermediates useful for preparing prostaglandin-type compounds with an alkoxy group replacing the hydroxyl at the C-15 position are disclosed. These products are useful for the same pharmacological properties as the unsubstituted prostaglandins.

9 Claims, No Drawings

BICYCLIC LACTONE INTERMEDIATES

CROSS REFERENCE TO RELATED APPLICATIONS

This application is a continuation of our copending application Ser. No. 326,642 filed Jan. 26, 1973, and now abandoned, which was a division of then copending application Ser. No. 140,251, filed May 4, 1971 and now abandoned.

DESCRIPTION OF THE INVENTION

This invention relates to compositions of matter, and to methods and intermediates for producing them. In particular, the several aspects of this invention relate to novel analogs of some of the known prostaglandins, for example, prostaglandin $E_1$ ($PGE_1$), prostaglandin $E_2$ ($PGE_2$), prostaglandin $E_3$ ($PGE_3$), prostaglandin $F_1$ ($PGF_{1\alpha}$ and $PGF_{1\beta}$), prostaglandin $F_2$ ($PGF_{2\alpha}$ and $PGF_{2\beta}$), prostaglandin $F_3$ ($PGF_{3\alpha}$ and $PGF_{3\beta}$), prostaglandin $A_1$ ($PGA_1$), prostaglandin $A_2$ ($PGA_2$), prostaglandin $A_3$ ($PGA_3$), prostaglandin $B_1$ ($PGB_1$), prostaglandin $B_2$ ($PGB_2$), and prostaglandin $B_3$ ($PGB_3$), and the dihydro derivatives of $PGE_1$, $PGF_{1\alpha}$, $PGF_{1\beta}$, $PGA_1$, and $PGB_1$, to novel methods for producing those novel prostaglandin analogs, and to novel chemical intermediates useful in those novel methods.

Each of the above-mentioned known prostaglandins is a derivative of prostanoic acid which has the following structure and atom numbering:

A systematic name for prostanoic acid is 7-[(2β-octyl)-cyclopent-1α-yl]heptanoic acid.

$PGE_1$ has the following structure:

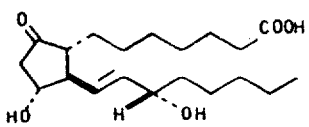

$PGF_{1\alpha}$ has the following structure:

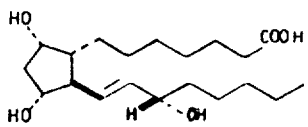

$PGF_{1\beta}$ has the following structure:

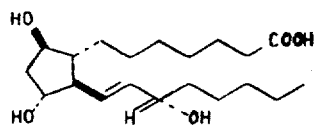

$PGA_1$ has the following structure:

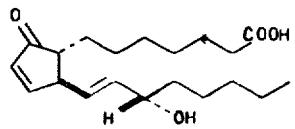

$PGB_1$ has the following structure

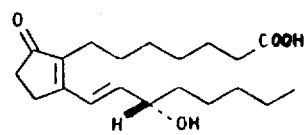

Each of the known prostaglandins $PGE_2$, $PGF_{2\alpha}$, $PGF_{2\beta}$, $PGA_2$, and $PGB_2$ has a structure the same as that shown for the corresponding $PG_1$ compound except that in each C-5 and C-6 are linked with a cis carbon-carbon double bond. For example, $PGE_2$ has the following structure:

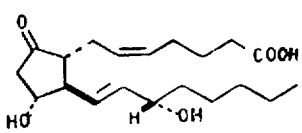

Each of the known prostaglandins, $PGE_3$, $PGF_{3\alpha}$ has a structure the same as that shown for the corresponding $PG_2$ compound except that, in each, C-17 and C-18 are linked with a cis carbon-carbon double bond. For example, $PGE_3$ has the following structure:

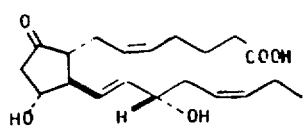

Each 13,14-dihydro derivative of $PGE_1$, $PGF_{1\alpha}$, $PGF_{1\beta}$, $PGA_1$, and $PGB_1$ has a structure the same as that shown for the corresponding $PG_1$ compound except that in each, C-13 and C-14 are linked with a carbon-carbon single bond. For example, dihydro-$PGE_1$ has the following structure:

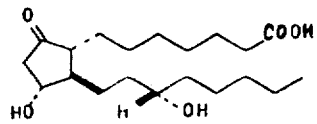

The prostaglandin formulas mentioned above each have several centers of asymmetry. Each formula represents the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the enantiomer of that prostaglandin. The racemic form of the prostaglandin consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins. For convenience hereinafter, use of the terms "$PGF_1$", "$PGF_{1\alpha}$", and the like, will mean the optically active form of that prostaglandin with the same absolute configuration as $PGE_1$ obtained from mammalian tissues.

When reference to the racemic form of either of these prostaglandins is intended, the word "racemic" will precede the prostaglandin name, thus, "racemic PGE₁" or "racemic PGF₁α", and the like.

In the formulas given above, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

Each of the novel prostanoic acid analogs of this invention is encompassed by the following formula or by the combination of that formula and its mirror image:

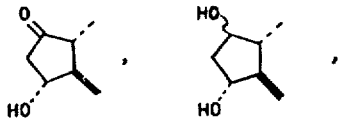

wherein D is one of the four carbocyclic moieties:

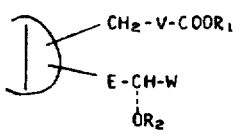

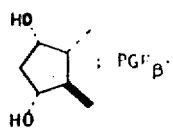

wherein E is —CH₂CH₂— or trans —CH=CH—; wherein R₁ is hydrogen, alkyl of one to 8 carbon atoms, inclusive, or a pharmacologically acceptable cation, and R₂ is alkyl of one to 5 carbon atoms, inclusive; wherein V is either —(CH₂)₅— or cis—CH=λ CH—(CH₂)₃—, provided that E is —CH₂CH₂— only where V is —(CH₂)₅—; wherein W is 1-pentyl or cis 1-pent-2-enyl provided that W is cis 1-pent-2-enyl only when E is trans—CH=CH— and V is —CH=λ CH—(CH₂)₃—; and wherein ~ indicates attachment of hydroxyl to the cyclopentane ring in alpha or beta configuration.

Formula I, which is written in generic form for convenience, represents PGE-type compounds when D is

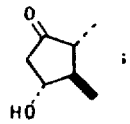

PGF<sub>α</sub> -type compounds when D is

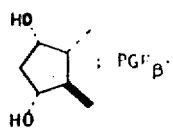

PGF<sub>β</sub> -type compounds when D is

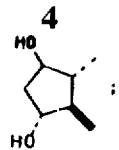

PGA-type compounds when D is

and PGB-type compounds when D is

Formula I represents PG₁-type compounds when E is trans—CH—CH—, V is —(CH₂)₅—, and W is 1-pentyl. PG₂-type compounds when E is trans—CH=CH—, V is cis—CH=CH—(CH₂(₃, and W is 1-pentyl; PG₃-type compounds when E is trans—CH=CH—, V is cis—CH=CH—(CH₂)₃—, and W is 1-pent-2-enyl, and 13,14-dihydro-PG₁-type compounds when E is —CH₂CH₂—, V is —(CH₂)₅—, and W is 1-pentyl. In Formula I, the configuration of the alkoxy (—OR₂) group at C-15 is alpha as is the hydroxy in the known prostaglandins discussed above.

The following formulas (II–XVII) represent the novel 15-alkyl ether prostaglandin analogs of this invention, wherein R₁ and R₂ are as defined above.

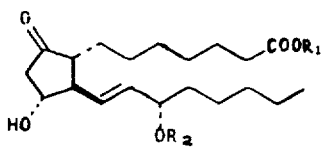

II

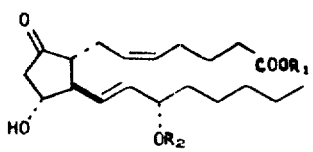

III

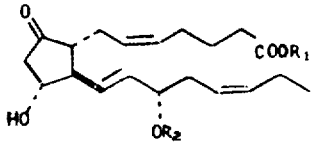

IV

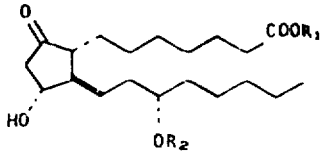

V

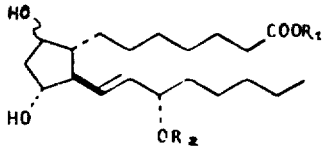

VI

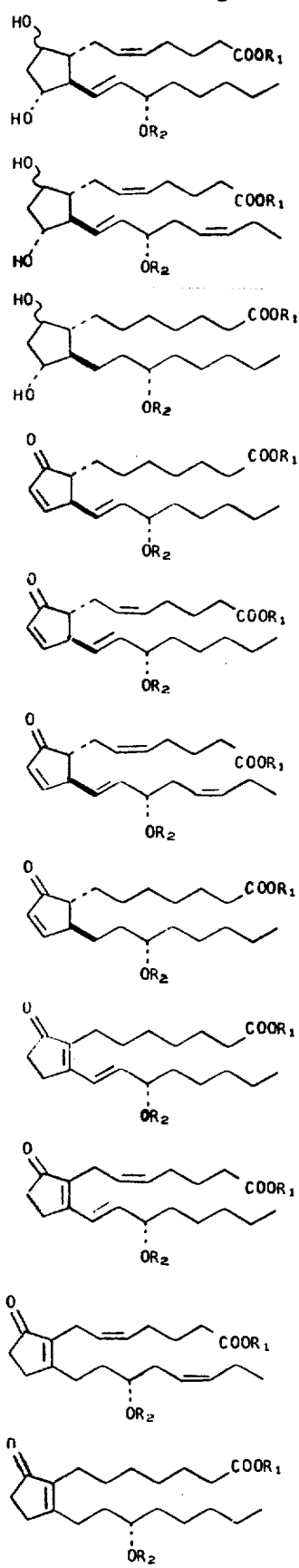

Each of the novel prostanoic acid analogs of this invention has an alkoxy group at the C-15 position, i.e. the position normally occupied by the side-chain hydroxyl of the naturally-occurring prostaglandins. Thus, these novel prostanoic acid analogs are conveniently designated as 15-alkyl ethers of the prostaglandins, e.g. "$PGE_1$, 15-methyl ether", and the like.

With regard to Formulas I–XVII, examples of alkyl of 1 to 5 carbon atoms, inclusive, are methyl, ethyl, propyl, butyl and pentyl, and isomeric forms thereof. Examples of alkyl of 1 to 8 carbon atoms, inclusive, include those 1 to 5 carbon atom alkyl groups and, in addition, hexyl, heptyl, and octyl, and isomeric forms thereof.

Like the natural prostaglandins described above, these novel 15-alkyl ethers prostaglandin compounds have several centers of asymmetry. As in the case of the formulas representing the prostaglandins, Formulas I through XVII, inclusive, are intended to represent optically active prostanoic acid analogs with the same absolute configurations as $PGE_1$ obtained from mammalian tissues. The novel prostanoic acid derivatives of this invention also include the corresponding racemic compounds. For example, Formula II and its mirror image are necessary in combination to describe the racemic $PGE_1$ compounds. For convenience hereinafter, when the word "racemic" procedes the name of one of the novel prostanoic acid derivatives of this invention, the intent is to designate a racemic compound represented by the combination of the appropriate Formula I through XVII and the mirror image of that formula. When the word "racemic" does not precede the compound name, the intent is to designate an optically active compound represented only by the appropriate Formula I through XVII and with the same absolute configuration as $PGE_1$ obtained from animal tissues.

$PGE_1$, $PGE_2$, $PGE_3$, and dihydro-$PGE_1$, and the corresponding $PGF_\alpha$, $PGF_\beta$, PGA, and PGB compounds, and their esters and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are systemic arterial blood pressure lowering in the case of the PGE and $PGF_\beta$ compounds as measured, for example, in anesthetized (pentobarbital sodium) pentolinium-treated rats with indwelling aortic and right heart cannulas; pressor activity, similarly measured, for the $PGF_\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 $\mu$g. to about 10 mg. per ml. of a pharmacologically suitable liquid vehicle or as an aerosol spray, both for topical application.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, PGF$_\alpha$, and PGF$_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$_\alpha$, and PGF$_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore PGE$_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediatly after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE and PGF$_\beta$ compounds are useful as hypotensive agents to reduce blood pressure in mammals including man. For this purpose, the compounds are administered by intravenous infusion at the rate about 0.01 to about 50 $\mu$g. per kg. of body weight per minute, or in single or multiple doses of about 25 to 500 $\mu$g. per kg. of body weight total per day.

The PGE, PGF$_\alpha$, and PGF$_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose 0.01 to 50 $\mu$g. per kg. of body weight per minute until or near the termination of the second stage of labor, i.e., expulsion of the fetus. These compounds are especially useful when the female is one or more weeks postmature and natural labor has not started, or 12 to 60 hours after the membranes have ruptured and natural labor has not yet started.

The PGE, PGF$_\alpha$, and PGF$_\beta$ compounds are useful for controlling the reproductive cycle in ovulating female mammals, including humans and other animals. For that purpose, PGF$_{2\alpha}$, for example, is administered systemically at a dose level in the range 0.01 mg. of about 20 mg. per kg. of body weight, advantageously during a span of time starting approximately at the time of ovulation and ending approximately at the time of menses or just prior to menses. Additionally, expulsion of an embryo or a fetus is accomplished by similar administration of the compound during the first third of the normal mammalian gestation period. Because the PGE compounds are potent antagonists of epinephrine-induced mobilization of free fatty acids, they are useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephretic states, the vasopressin action of these compounds is especially useful. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous, intramuscular, or subcutaneous injection or infusion in the range 0.05 to 2 mg. per kg. of body weight per day.

The PGE and PGB compounds promote and accelerate the growth of epidermal cells and keratin in animals, including humans, and other animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 $\mu$g./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

The novel Formula II-to-V PGE-type compounds, the novel Formula VI-to-IX PGF$_\alpha$-type and PGF$_\beta$-type compounds, the novel Formula X-to-XIII PGA-type compounds, and the novel Formula XIV-to-XVII PGB-type compounds each cause the biological responses described above for the PGE, PGF$_\alpha$, PGF$_\beta$, PGA, and PGB compounds respectively, and each of these novel compounds is accordingly useful for the above-described corresponding purposes, and is used for those purposes in the same manner as described above.

The known PGE, PGF$_\alpha$, PGF$_\beta$, PGA, and PGB compounds are all potent in causing multiple biological responses even at low doses. For example, PGE$_1$ and PGE$_2$ are extremely potent in causing vasodepression and smooth muscle stimulation, and also are potent as antilipolytic agents. Moreover, for many applications, these known prostaglandins have an inconveniently short duration of biological activity. In striking contrast, the novel prostaglandin analogs of Formulas II to XVII are substantially more specific with regard to potency in causing prostaglandin-like biological responses, and have a substantially longer duration of biological activity. Therefore, each of these novel prostaglandin analogs is surprisingly and unexpectedly more useful than one of the corresponding above-mentioned known prostaglandins for at least one of the pharmacological purposes indicated above for the latter, because it has a different and narrower spectrum of biological activity than the known prostaglandins, and therefore is more specific in its activity and causes smaller and fewer undesired side effects than the known prostaglandins. Moreover, because of its prolonged activity, fewer and smaller doses of the novel prostaglandin analog can frequently be used to attain the desired result.

Another advantage of the novel compounds of this invention, compared with the known prostaglandins, is that these novel compounds are administered effectively orally, sublingually, intravaginally, buccally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

Theh 15-alkyl ether PGE, PGF$_\alpha$, PGF$_\beta$, PGA, and PGB type compounds encompassed by Formulas II through XVII above are used for the purposes described above in the free acid form, in ester form, or in pharmacologically acceptable salt form. When the ester form is used, the ester is any of those within the above definition of R$_1$. However, it is preferred that the ester be alkyl of one to four carbon atoms, inclusive. Of those alkyl, methyl, and ethyl are especially preferred for optimum absorption of the compound by the body or experimental animal system.

Pharmacologically acceptable salts of these Formula II-to-XVII compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

As discussed above, the compounds of Formulas II through XVII are administered in various ways for various purposes; e.g., intravenously, intramuscularly, subcutaneously, orally, intravaginally, rectally, bucally, sublingually, topically, and in the form of sterile implants for prolonged action.

For intravenous injection or infusion, sterile aqueous isotonic solutions are preferred. For that purpose, it is preferred because of increased water solubility that $R_1$ in the Formula II-to-XVII compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixers, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used.

The 15-alkyl ether prostaglandin-type compounds encompassed by Formulas I through XVII inclusive, are produced by the reactions and procedures described and exemplified hereinafter.

Referring to Charts A and B, the 15-alkyl ether $PGE_2$ compounds of Formula XXXI are produced from alkyl ether intermediates of Formula XXVI.

CHART A

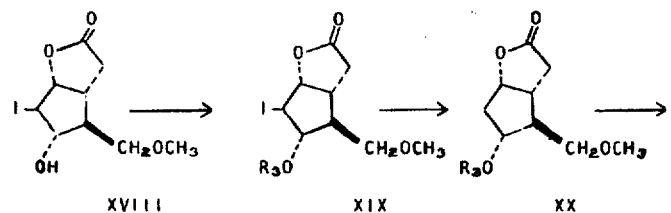

XVIII     XIX     XX

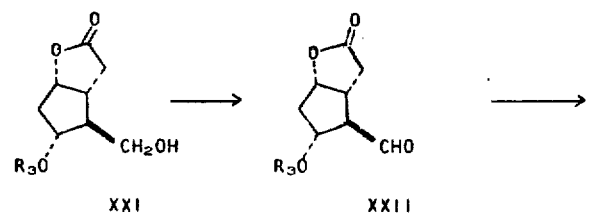

XXI     XXII

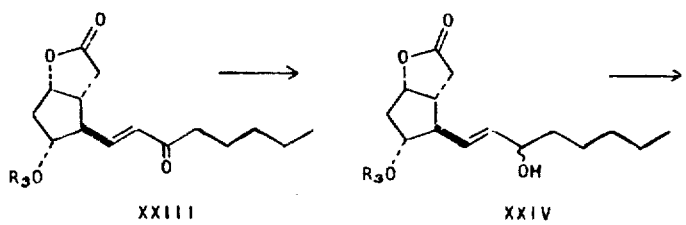

XXIII     XXIV

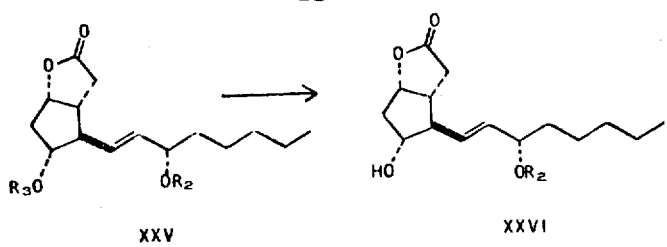

CHART B

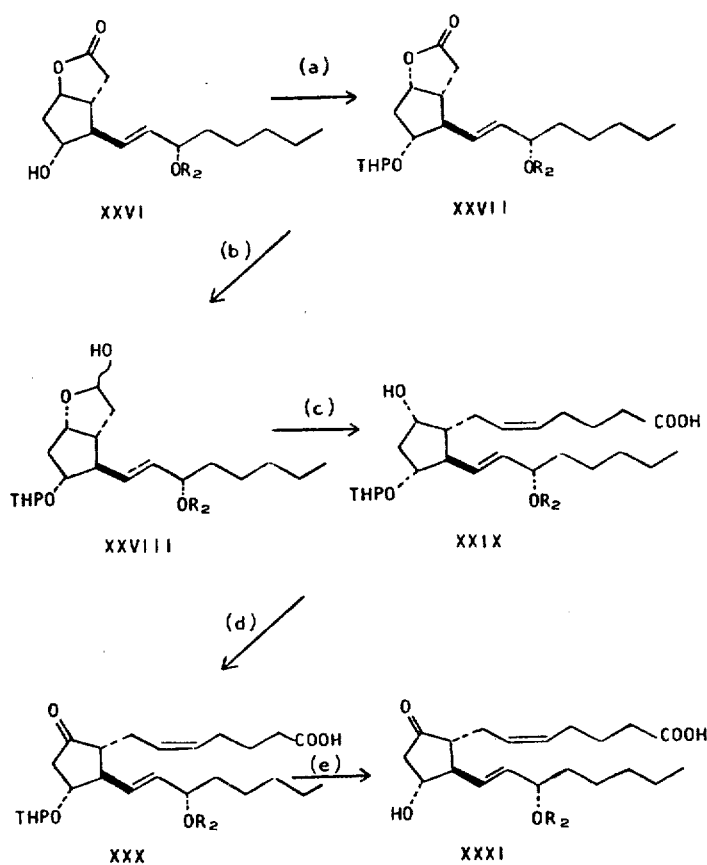

Therein, and throughout this disclosure, $R_2$ is alkyl of one to 5 carbon atoms, inclusive, the most preferred forms of alkyl being methyl and ethyl. The Formula-XXVI intermediates are prepared by the sequence of steps shown in Chart A, using intermediates XIX through XXV wherein $R_3$ is either benzoyl or acetyl. Generally for ease in purification, and for economies and higher yields, benzoyl is preferred.

In Charts A and B, as in subsequent Charts herein, the formulas as depicted represent optically active compounds. The same sequence of steps is applicable to the racemic compounds consisting of the optically active compounds as depicted and the mirror images thereof, thereby yielding the racemic intermediates and thence the racemic PG products.

Previously, the preparation of an intermediate bicyclic lactone diol of the formula

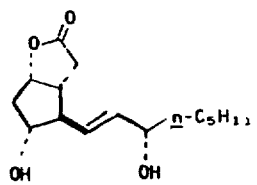

was reported by E. J. Corey et al., J. Am. Chem. Soc. 91, 5675 (1969), and later disclosed in an optically active form by E. J. Corey et al., J. Am. Chem. Soc. 92, 397 (1970). Conversion of this intermediate to $PGE_2$ and $PGF_{2\alpha}$, either in racemic or optically active form, was disclosed in those publications. Conversion to $PGE_3$ and $PGF_{3\alpha}$ was disclosed by Corey et al., J. Am. Chem. Soc. 93, 1490 (1971).

The iodolactone of Formula XVIII in Chart A is known in the art (see Corey et al., above). It is available in either racemic or optically active (+ or −) form. for racemic products, the racemic form is used. For prostaglandins of natural configuration, the laevorotatory form (−) is used.

The Formula-XIX compound bears an $R_3O$- moiety at the 4-position, wherein $R_3$ is as defined above. In preparing the Formula-XIX compound by replacing the hydrogen of the hydroxyl group in the 4-position with the acyl group $R_3$, methods known in the art are used. Thus, if $R_3$ is benzoyl, benzoic acid is reacted with the Formula-XVIII compound in the presence of a dehydrating agent, e.g. sulfuric acid, zinc chloride, or phosphoryl chloride; or benzoic anhydride is used.

Preferably, however, an acyl halide, for example benzoyl chloride or acetyl chloride, is reacted with the Formula-XVIII compound in the presence of a hydrogen chloride-scavenger, e.g. a tertiary amine such as pyridine, triethylamine, and the like. The reaction is carried out under a variety of conditions using procedures generally known in the art. Generally, mild conditions are employed, e.g. 20°–60° C., contacting the reactants in a liquid medium, e.g. excess pyridine or an inert solvent such as benzene, toluene or chloroform. The acylating agent is used either in stoichiometric amount or in excess.

The Formula-XX compound is next obtained by deiodination of XIX using a reagent which does not react with the lactone ring or the $OR_3$ moiety, e.g. zinc dust, sodium hydride, hydrazine-palladium, hydrogen and Raney nickel or platinum, and the like. Especially preferred is tributyltin hydride in benzene at about 25° C. with 2,2'-azobis-(2-methylpropionitrile) as initiator.

The Formula-XXI compound is obtained by demethylation of XX with a reagent that does not attack the $OR_3$ moiety, for example boron tribromide or trichloride. The reaction is carried out preferably in an inert solvent at about 0°–5° C.

The Formula-XXII compound is obtained by oxidation of the $-CH_2OH$ of XXI to $-CHO$, avoiding decomposition of the lactone ring. Useful for this purpose are dichromate-sulfuric acid, Jones reagent, lead tetraacetate, and the like. Especially preferred is Collins' reagent (pyridine-$CrO_3$) at about 0°–10° C.

The Formula-XXIII compound is obtained by Wittig alkylation of XXII, using the sodio derivative of dimethyl 2-oxoheptylphosphonate. the trans enone lactone is obtained stereospecifically (see D. H. Wadsworth et al., J. Org. Chem. Vol. 30, p. 680 (1965)).

The Formula-XXIV compound is obtained by reduction of XXIII, yielding a mixture of alpha and beta isomers. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides. lithium (tri-tert-butoxy)aluminum hydride, metal trialkoxy borohydrides, e.g., sodium trimethoxyborohydride, lithium borohydride, diisobutyl aluminum hydride, and when carbon-carbon double bond reduction is not a problem, the boranes, e.g., disiamylborane.

For production of natural-configuration PG-type analogs, the desired alpha form of the Formula-XXIV compound is separated from the beta isomer by silica gel chromatography.

The Formula-XXV compound is prepared by alkylation of the side-chain hydroxy of the Formula-XXIV compound thereby replacing hydroxy with the $-OR_2$ moiety. For this purpose, diazoalkanes may be employed, preferably in the presence of a Lewis Acid, e.g. boron trifluoride etherate, aluminum chloride, or fluoboric acid. When $R_2$ is methyl, diazomethane is used. See Fieser et al., "Reagents for Organic Synthesis", John Wiley and Sons, Inc. N.Y. (1967), p. 191. Other $-OR_2$ groups are formed by using the corresponding diazoalkane. For example diazoethane and diazobutane yield $-OC_2H_5$ and $-OC_4H_9$ respectively. The reaction is carried out by mixing a solution of the diazoalkane in a suitable inert solvent, preferably ethyl ether, with the Formula-XXIV compound. Generally the reaction proceeds at about 25° C. Diazoalkanes are known in the art or can be prepared by methods known in the art. See, for example, Organic Reactions, John Wiley and Sons, Inc., N.Y. Vol. 8, pp. 389–394 (1954).

Another method for the alkylation of the side chain hydroxy is by the reaction of an alcohol in the presence of boron trifluoride etherate. Thus, methanol and boron trifluoride etherate yield the methyl ether wherein $R_2$ is methyl. The reaction is done at about 25° C. and is conveniently followed with thin layer chromatography (TLC).

Another method for the alkylation of the side-chain hydroxy is by the reaction of an alkyl halide, e.g. methyl iodide, in the presence of a metal oxide or hydroxide, e.g. barium oxide, silver oxide, or barium hydroxide. An inert solvent may be beneficial, for example benzene or dimethylformamide. The reactants are preferably stirred together and maintained at temperatures of 25°–75° C.

Still another method is by first converting the hydroxy to mesyloxy (i.e. methanesulfonate) or tosyloxy (i.e. toluenesulfonate) and thence transforming the mesyloxy or tosyloxy to the $-OR_2$ moiety by reaction with a metal alkoxide, e.g. potassium tert-butoxide. The mesylate or tosylate is prepared by reaction of the Formula-XXIV intermediate with either methanesulfonyl chloride or toluenesulfonyl chloride in pyridine. Thereafter, the mesylate or tosylate is mixed with the appropriate potassium or sodium alkoxide in pyridine, the reaction proceeding smoothly at about 25° C. An equivalent amount of the alkoxide based on the mesylate is preferred to avoid side reactions. In this manner, the Formula-XXV intermediate is prepared wherein $R_2$ is normal alkyl, secondary alkyl or tertiary alkyl of 1 to 5 carbon atoms. The method is especially useful for tertiary alkyl substitutions for hydrogen, e.g. where $R_2$ is tert-butyl or tert-pentyl.

The Formula-XXVI compound is then obtained by deacylation of XXV with an alkali metal carbonate, for example potassium carbonate in methanol at about 25° C.

The process for producing a compound of the formula

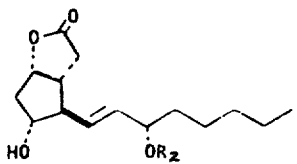

wherein $R_2$ is as defined above therefore comprises starting with a compound of the formula

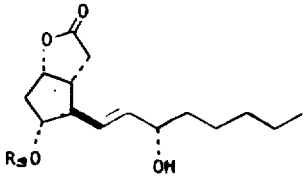

wherein $R_3$ is as defined above, replacing the hydroxy with the —$OR_2$ moiety, and thereafter replacing the —$OR_3$ moiety with hydroxy.

The transforamtions of the Formula-XXVI compounds to the Formula-XXXI $PGE_2$-type compounds are shown in Chart B. The Formula-XXXI products fall within the scope of Formula-III.

In step a, the tetrahydropyranyl ether XXVII is obtained by replacing the ring hydroxyl with tetrahydropyranyloxy. To accomplish this, the formula-XXVI compound is reacted with dihydropyran in an inert solvent, e.g. dichloromethane, in the presence of an acid condensing agent such as p-toluenesulfonic acid. The dihydropyran is used in excess, preferably 4 to 10 times theory. The reaction is normally complete in 15–30 min. at 20°–30° C.

In step b, the lactol XXVIII is obtained on reduction of the oxo of the Formula-XXVII lactone without reducing the 13,14-ethylenic group. For this purpose, diisobutyl-aluminum hydride is preferred. The reduction is preferably done at —60° to —70° C.

In step c, the Formula-XXIX compound is obtained by a Wittig alkylation, using a Wittig reagent derived from 4-carboxybutyl triphenylphosphonium bromide, and sodio dimethylsulfinylcarbanide. the Wittig reagent is prepared from an intermediate Hal—$(CH_2)_4$—COOH compound wherein Hal is chloro or bromo by methods known in the art. See, for example, Fieser et al., op. cit. pp 1238–1242. The reaction with the Formula-XXVIII lactol occurs readily at about 25° C. This Formula-XXIX compound serves as an intermediate for preparing either the $PGE_2$-type or the $PGF_{-2\alpha}$ -type products, Charts B and C respectively.

To prepare the Formula-XXXI (III) $PGE_2$-type compounds, the Formula-XXIX tetrahydropyranyl ether is oxidized at the 9-hydroxy position, preferably with Jones reagent, to form 9-oxo, step d. Finally, in step e, the tetrahydropyranyl groups are replaced with hydrogen, by hydrolysis, e.g. with methanol/HCl or with acetic acid/water/tetrahydrofuran at 40°–55° C. thereby avoiding formation of $PGA_2$-type compounds as by-products.

There is therefore provided a process for producing a $PGE_2$-type compound of the formula

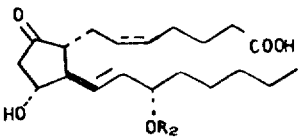

wherein $R_2$ is as defined above, which comprises starting with a reactant of the formula

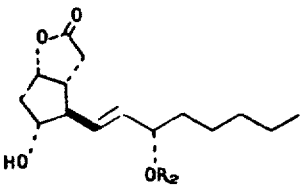

and subjecting it successively to the steps of
a. replacement of free ring hydroxyl with tetrahydropyranyloxy;
b. reduction of the lactone oxo to hydroxy;
c. Wittig alkylation with a compound of the formula Hal—$(CH_2)_4$—COOH wherein Hal is bromo or chloro;
d. oxidation of 9-hydroxy to oxo; and
e. transformation of tetrahydropyranyloxy to hydroxy.

In like manner the racemic product consisting of the Formula-XXXI compound and its mirror image is produced by starting with a racemic reactant consisting of the Formula-XXVI compound and its mirror image.

In Chart C are shown the transformations of the Formula-XXVI compounds to $PGF_{2\alpha}$ -type compounds of Formula XXXII, which are within the scope of Formula VII when ~ is alpha.

The Formula-XXVI starting material is transformed to the Formula-XXIX intermediate by the steps described above and illustrated in Chart B, steps a through c. The tetrahydropyranyloxy group of the Formula-XXIX compound is then replaced with hydroxy by hydrolysis, e.g., with methanol/HCl or with acetic acid/water/tetrahydrofuran at 40°–55° C. to yield the Formula-XXXII product.

There is therefore provided a process for producing a $PGF_{2\alpha}$ -type compound of the formula

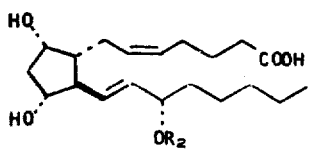

wherein $R_2$ is as defined above which comprises starting with a reactant of the formula

CHART C

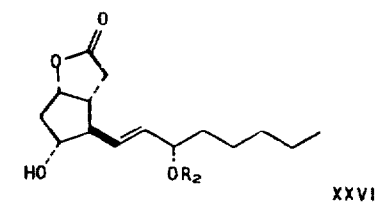
XXVI

↓ by way of steps a-c of Chart B

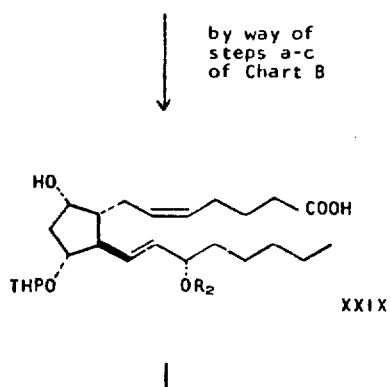
XXIX

↓

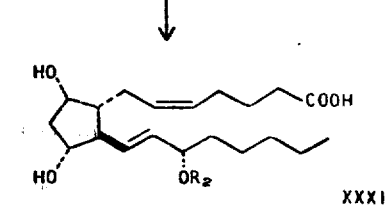
XXXII

↓

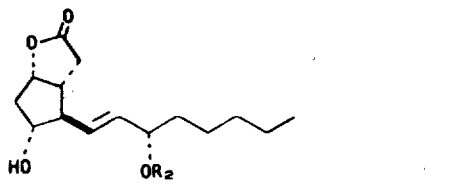
XXVI and subjecting it successively to the steps of
a. replacement of ring hydroxyl with tetrahydropyranyloxy;
b. reduction of the lactone oxo to hydroxy;
c. Wittig alkylation with a compound of the formula Hal—$(CH_2)_4$—COOH wherein Hal is bromo or chloro; and
d. transformation of tetrahydropyranyloxy to hydroxy.

In like manner, the racemic product consisting of the Formula-XXXII compound and its mirror image is produced by starting with a racemic consisting of the Formula-XXVI compound and its mirror image.

In Chart D is shown a general method for preparing the Formula-XXXIV alkyl ester 15alkyl ether compounds and thence the Formula-XXXV free acid 15-alkyl ether compounds useful per se or for preparing esters or salts.

The reactant compounds encompassed by Formula XXXIII of Chart D are the free acids and alkyl esters fo the $PG_1$ compounds of PGE, PGFα, PGFβ, PGA, and PGB, and also the corresponding $PG_2$, $PG_3$, and 13,14-dihydro-$PG_1$ compounds. In generic Formula XXXIII, the symbols D, E, $R_1$, V, and W are as defined above.

The initial optically active reactants of Formula XXXIII in Chart D are known in the art or are prepared by methods known in the art.

CHART D

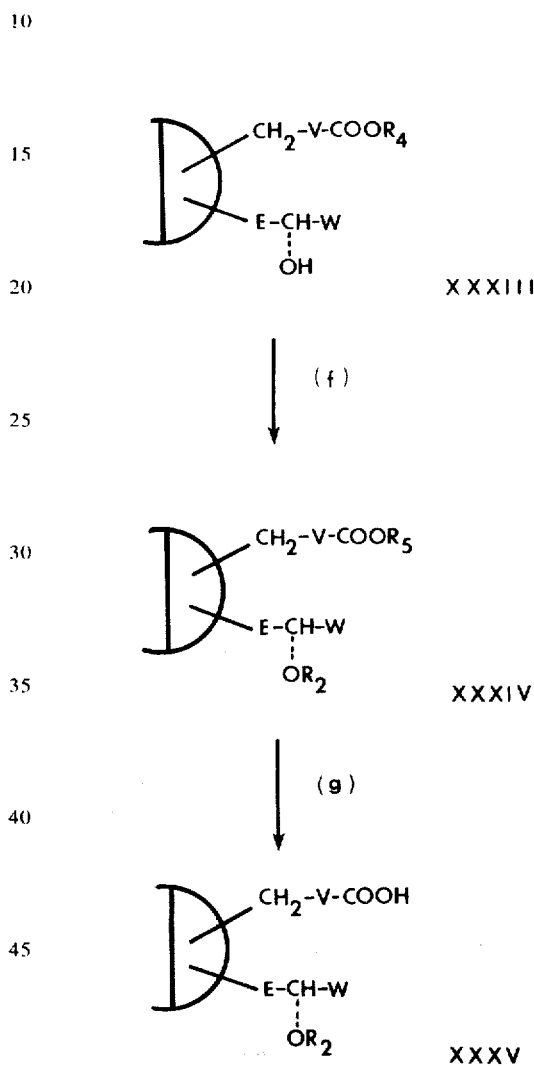

See, for example, Bergstrom et al., Pharmacol, Rev. 20, 1 (1968); U.S. Pat. No. 3,069,322; British Specification No. 1,040,544; Corey et al., 1. Am. Chem. Soc. 92, 397 (1970), 92, 2586 (1970), and 93, 1490 (1971). The initial racemic reactants of Formula XXXIII in Chart D are known in the art or are prepared by methods known in the art. See for example, Just et al., J. Am. Chem. Soc. 91, 5364 (1969), Corey et al., J. Am. Chem. Soc. 90, 3245 (1968), and 91, 5675 (1969), Schneider et al., Chem. Commun, (Great Britain), 304 (1969), and Axen et al., Chem. Commun. (Great Britain), 602 (1970).

In step f of Chart D the various PGE and PGF compounds encompassed by Formula XXXIII and its mirror image are subjected to monoalkylation so that the C-15 hydroxyls are thereby converted to C-15 alkyl ether groups within the scope of this invention, i.e. —$OR_2$ moieties wherein $R_2$ is as defined above. For this purpose, the methods discussed above in alkylating the Formula-XXIV compounds to replace —OH with —OR$_2$ are useful. Thus, either (1) diazoalkanes, e.g. diazomethane, (2) alkyl halides, e.g. methyl iodide, ethyl chloride, and the like, with silver oxide or (3) metal alkoxides are employed. The conditions are generally the same as those used for forming the —OR$_2$ moiety on the Formula-XXV compounds of Chart A, discussed above, except that the reactions are controlled to minimize the formation of impurities and by-products. The duration of the reaction for various reaction conditions, e.g. temperature, concentration, agitation, presence of catalysts, and the like, is optimized for the C-15 alkyl ether simply by following the course of the reaction by thin layer chromatography (TLC) and observing the production of that C-15 ether in comparison with the formation of undesired by-products and impurities. The monohydroxy PGA and PGB compounds are not as likely to yield by-products.

The desired 15-alkyl ethers are separated from the reaction mixture impurities and unreacted starting material by methods known in the art, for example silica gel chromatography, including thin layer and column chromatography, and countercurrent distribution procedures. See Ramwell and Daniels, "Chromatography of the Prostaglandins", in "Lipid Chromatographic Analysis", Vol. 2, G. V. Marinetti, ed., Marcel Dekker, Inc., N.Y., 1969.

Generally the free carboxyl groups of the Formula-XXXIII reactants wherein R$_4$ is hydrogen are also esterified in this process, so that the corresponding alkyl esters are produced rather than the free acid. In Formula XXXIV, R$_5$ is alkyl of 1 to 8 carbon atoms, inclusive. In step g, the Formula-XXXV free acid alkyl ethers are formed from the Formula-XXXIV esters by several methods, For the PGF and PGB compounds, saponification may be employed, e.g. with sodium or potassium hydroxide, using methods known in the art. For the PGE and PGA compounds, which are sensitive to the normally alkaline conditions used for saponification, other methods known in the art for converting esters to acids are required. Especially preferred is enzymatic hydrolysis, discussed in more detail below.

There is therefore provided a process for producing a compound of the formula

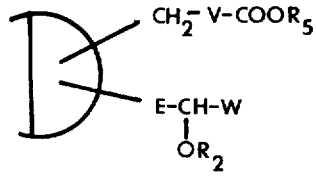

wherein D, E, R$_2$, R$_5$, V, and W are as defined above, which comprises starting with a reactant of the formula

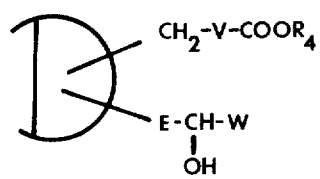

wherein D, E, R$_4$, V, and W are as defined above, replacing the side-chain hydroxy with the —OR$_2$ moiety wherein R$_2$ is as defined above, and separating the alkyl ether product compound from the reaction mixture.

In like manner, the racemic product consisting of the Formula-XXXIV compound and its mirror image is produced by starting with a racemic reactant consisting of the Formula-XXXIII compound and its mirror image.

In addition to the methods described above, reference to Chart E will show other useful methods.

The various PGF$_\alpha$ -type and PGF$_\beta$ -type compounds encompassed by Formulas VI to IX (XXXVII, Chart E) are prepared by carbonyl reduction of the corresponding PGE-type compounds (XXXVI, Chart E.). For example, carbonyl reduction of PGE$_2$, 15-methyl ether gives a mixture of PGF$_2$ $_\alpha$ , 15-methyl ether, and PGF$_2$ $_\beta$ , 15-methyl ether.

These ring carbonyl reductions are carried out by methods known in the art for ring carbonyl reductions of known prostanoic acid derivatives. See, for example, Bergstrom et al., Arkiv Kemi 19, 563 (1963), Acta. Chem. Scand. 16, 969 (1962), and British Specification No. 1,097,533. Any reducing agent is used which does not react with carbon-carbon double bonds or ester groups.

CHART E

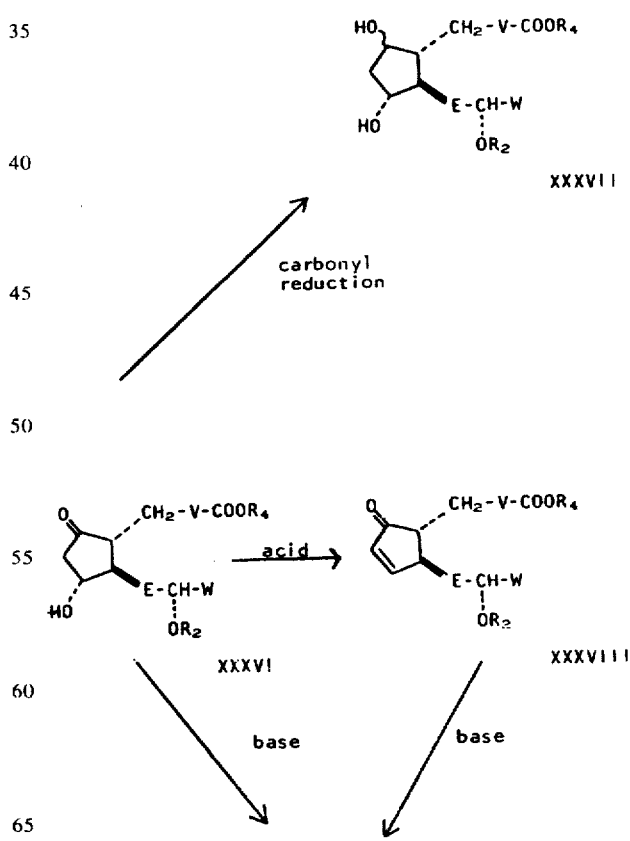

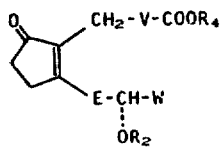

XXXIX

Preferred reagents are lithium (tri-tert-butoxy)aluminum hydride, the metal borohydrides, especially sodium, potassium and zinc borohydrides, and the metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research 5, 117 (1964). Especially preferred as separation methods are partition chromatographic procedures, both normal and reversed phase, preparative thin layer chromatography, and countercurrent distribution procedures.

The various PGA-type compounds encompassed by Formulas X to XIII (XXXVIII, Chart E) are prepared by acidic dehydration of the corresponding PGE type compounds. For example, acidic dehydration of PGE$_2$, 15-ethyl ether gives PGA$_2$, 15-ethyl ether.

These acidic dehydrations are carried out by methods known in the art for acidic dehydrations of known prostanoic acid derivatives. See, for example, Pike et al., Proc. Nobel Symposium II, Stockholm (1966), Intersceince Publishers, New York, pp. 162–163 (1967); and British Specification 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may cause partial hydrolysis of an ester reactant.

The various PGB-type compounds encompassed by Formulas XIV to XVII (XXXIX, Chart E) are prepared by basic dehydration of the corresponding PGE-type compounds, or by contacting the corresponding PGA-type compounds with base. For example, both PGE$_1$, 15-methyl ether and PGA$_1$, 15-methyl ether give PGB$_1$, 15-methyl ether, on treatment with base.

These basic dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The PGE-type or PGA-type compound is maintained in such a reaction medium until no further PGB-type compound is formed, as shown by the characteristic untraviolet light absorption near 278 μ for the PGB-type compound.

In Chart E, the various symbols, E, R$_2$, R$_4$, V, W, and ~ have the same means ascribed to them above. The reaction steps shown for the compounds in Chart E are also applicable to the racemic compounds consisting of the optically active compounds as depicted and the mirror images thereof, thereby yielding the racemic PGF, PGA, and PGB products.

In Chart F is shown a preferred methods for transforming PGE compounds to PGF compounds, and especially PGF$_\alpha$ compounds.

CHART F

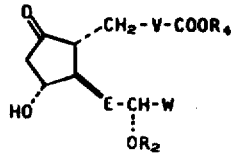

XXXVI

↓ (h)

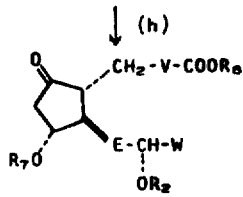

XL

↓ (i)

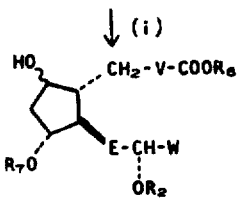

XLI

↓ (j)

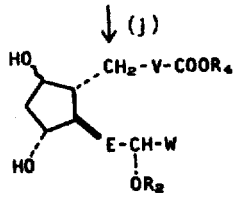

XXXVII

↓ (k)

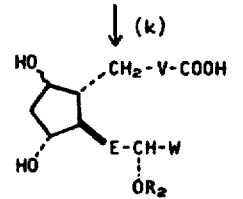

XLII

Therein, Formulas XXXVI to XLII represent optically active compound, and E, $R_2$, $R_4$, V, W, and ~ are as defined above; $R_6$ is either alkyl of one to 8 carbon atoms, inclusive, or $(A)_3$—Si— wherein A is alkyl of 1 to 4 carbon atoms, inclusive, phenyl, phenyl substituted with 1 or 2 fluoro, chloro, or alkyl of 1 to 4 carbon atoms, inclusive, or aralkyl of 7 to 12 carbon atoms, inclusive; and $R_7$ is either hydrogen or $(A)_3$—Si— as defined above. The same sequence of steps is applicable to the racemic compounds consisting of the optically active compounds as shown and the mirror images thereof.

The various PGF-type 15-alkyl ether compounds encompassed by Formula XLII are prepared by carbonyl reduction of the Formula-XXXVI PGE-type 15-alkyl ether compounds or their alkyl esters. Although the Formula-XXXVI compounds, and their racemic compounds with mirror images thereof, may be reduced directly to the corresponding Formula-XXXVII compounds, it may be preferred for a high ratio of the $PGF_\alpha$ -type compounds over the co-formed $PGF_\beta$ compounds to transform the 11-hydroxy groups to $(A)_s$—Si—O—moieties, as defined above, by silylation prior to the reduction step. The various A's of a —Si—$(A)_3$ moiety are alike or different. For example, —Si—$(A)_3$ can be trimethylsilyl, dimethylphenylsilyl, or methylphenylbenzylsilyl.

Referring to Chart F, the Formula-XL and -XLI compounds may be (1) esters, i.e. where $R_4$ of the Formula-XXXVI compound is alkyl, $R_6$ is also alkyl; (2) acids, i.e. derived from acid-form Formula-XXXVI compounds without silylation, whereby $R_6$ is hydrogen; or (3) silylated, whereby $R_6$ is $(A)_3$—Si— as above defined. If, as is preferred, the Formula-XXXVI compounds are subjected to silylation prior to reduction, $R_7$ is $(A)_3$—Si—; if not silylated, $R_7$ is hydrogen.

Silylation is accomplished by procedures known in the art. See, for example, Pierce, "Silylation of Organic Compounds," Pierce Chemical Co., Rockford, Ill. (1968). Sufficient silylating agent is used to transform the 11-hydroxy groups to $(A)_3$—Si—O moieties. As to the silylating agents known in the art, see, for example, Post, "Silicones and Other Organic Silicon Compounds," Reinhold Publishing Corp., New York, N.Y. (1949).

When the acid-form Formula-XXXVI compounds are used, excess silylating agent and prolonged treatment also transforms the —COOH to —COO—Si—$(A)_3$. It is optional whether or not the —COOH of the Formula-XXXVI reactants is esterified to —COO—Si—$(A)_3$.

Referring again to Chart F, step i, in the preferred process the mono- or disilylated Formula-XL PGE-type intermediates are reduced to the corresponding silylated Formula-XLI PGF-type compounds. These ring carbonyl reductions are carried out by methods known in the art, as discussed above in connection with Chart E.

Following the reduction, the silylated Formula-XLI PGF-type intermediates are hydrolyzed, in step j, to the corresponding Formula-XXXVII comounds wherein $R_6$ and $R_7$ silyl groups are replaced with hydrogen. These hydrolyses are carried out by prior art procedures known to be useful for transforming silyl ethers and silyl esters to alcohols and carboxylic acids, respectively. See, for example, Pierce, cited above, especially . 447 thereof. A mixture of water and sufficient of a water-miscible organic diluent to give a homogeneous hydrolysis reaction mixture represents a suitable reaction medium. Addition of a catalytic amount of an organic or inorganic acid hastens the hydrolysis. The length of time required for the hydrolysis is determined in part by the hydrolysis temperature. With a mixture of water and methanol at 25° C., several hours is usually sufficient for hydrolysis. At 0° C., several days is usually necessary.

The mixtures of PGF-type alpha and beta hydroxy reduction products are separated into the individual Formula-XXXVII alpha and beta isomers by methods known in the art.

Finally in step k of Chart F, the PGF-type esters of Formula XXXVII are hydrolyzed or saponified to the Formula-XLII free acids by the usual known procedures, as discussed above.

The PGF-type acids provide a route for the preparation of PGF-type acids.

The PGF-type 15-alkyl ether free acids are obtained on oxidation of the corresponding PGF-type 15-alkyl ether free acid compounds. Oxidation reagents useful for this transformation are known to the art. An especially useful reagent for this purpose is the Jones reagent, i.e., acidified chromic acid. See J. Chem. Soc. 39 (1946). Acetone is a suitable diluent for this purpose, and a slight excess beyond the amount necessary to oxidize one of the secondary hydroxy groups of the PGF reactant is used. Reaction temperatures at least as low as about 0° C. should be used. Preferred reaction temperatures are in the range −10° to −50° C. The oxidation proceeds rapidly and is usually complete in about 5 to 20 minutes. The excess oxidant is destroyed, for example by addition of a lower alkanol, advantageously, isopropyl alcohol, and the PGE-type 15-alkyl ether product is isolated by conventional methods.

Examples of other oxidation reagents useful for this transformation are silver carbonate on Celite (Chem. Commun. 1102 (1969)), mixtures of chromium trioxide and pyridine (Tetrahedron Letters 3363 (1968), J. Am. Chem. Soc. 75, 422 (1953), and Tetrahedron, 18, 1351 (1962)), mixtures of sulfur trioxide in pyridine and dimethyl sulfoxide (J. Am. Chem. Cos. 89, 5505 (1967)), and mixtures of dicyclohexylcarbodiimide and dimethyl sulfoxide (J. Am. Chem. Soc. 87, 5661 (1965)).

The various 13,14-dihydro-$PGE_1$-type, $-PGF_{1\alpha}$ -type, $-PGF_{1\alpha}$ -type, -$PGA_1$-type and -$PGB_1$-type, 15-alkyl ether compounds encompassed by Formulas V, IX, XIII, and XVII are prepared by carbon-carbon double bond reduction of the corresponding $PGE_1$, $PGF_{1\alpha}$ , $PGF_1\beta$ , $PGA_1$ , and $PGB_1$-type compound containing a trans 13,14-double bond in the hydroxy-containing side chain. A cis or trans double bond can also be present in the carboxy-terminated side chain of the unsaturated reactant, as in $PG_2$-type compounds and will be reduced at the same time to —$CH_2CH_2$—. Likewise, a 17,18- double bond in the $PG_3$-type compounds will be reduced to the —$CH_2CH_2$— moiety.

These reductions are carried out by reacting the unsaturated PGE, $PGF_\alpha$ , $PGF\beta$ , PGA, or PGB type 15-alkyl ether compound with diimide, following the general procedure described by van Tamelen et al., J. Am. Chem. Soc. 83, 3725 (1961). See also Fieser et al., "Topics in Organic Chemistry," Reinhold Publishing Corp., New York, pp. 432–434 (1963) and references cited therein. The unsaturated acid or ester reactant is mixed with a salt of azodiformic acid, preferably an alkali metal salt such as the disodium or dipotassium salt, in the presence of an inert diluent, preferably a lower alkanol such as methanol or ethanol, and preferably in the absence of substantial amounts of water. At least one molecular equivalent of the azodiformic acid salt is used for each multiple bond equivalent of the unsaturated reactant. The resulting suspension is then stirred, preferably with exclusion of oxygen, and the mixture is made acid, advantageously with a carboxylic acid such as acetic acid. When a reactant wherein $R_1$ is hydrogen is used, the carboxylic acid reactant also serves to acidify an equivalent amount of the azodiformic acid salt. A reaction temperature in the range of about 10° to about 40° C. is usually suitable. Within that temperature range, the reaction is usually complete within less than 24 hours. The desired dihydro product is then isolated by conventional methods, for example, evaporation of the diluent, followed by separation from inorganic materials by solvent extraction.

In the case of the unsaturated PGE, $PGF_\alpha$, and PGB $\beta$ -type reactants, the reductions to the corresponding 13,14-dihydro-$PGE_1$, dihydro-$PGF_{1\alpha}$, and dihydro-$PGF_{1\beta}$ -type compounds are also carried out by catalytic hydrogenation. For that purpose, palladium catalysts, especially on a carbon carrier, are preferred. It is also preferred that the hydrogenation be carried out in the presence of an inert liquid diluent, for example, methanol, ethanol, dioxane, ethyl acetate, and the like. Hydrogenation pressures ranging from about atmospheric to about 50 p.s.i., and hydrogenation temperatures ranging from about 10° to about 100° C. are preferred. The resulting 13,14-dihydro product is isolated from the hydrogenation reaction mixture by conventional methods, for example, removal of the catalyst by filtration or centrifugation, followed by evaporation of the solvent.

Diimide reductions and catalytic hydrogenations to produce the various novel Formula-V, -IX, -XIII, and -XVII 13,14-dihydro compounds of this invention from the corresponding PGE, PGF, $PGF_\beta$, PGA, and PGB type compounds of the $PG_1$, $PG_2$, and $PG_3$ series are shown in Chart G, wherein D, $R_2$, $R_4$, V, and W are as defined above.

The free-acid forms of the Formula-II-to-V-type compounds are prepared from their alkyl esters by enzymatic hydrolysis as follows. This procedure comprises subjecting their alkyl esters to the acylase enzyme system of a micro-organism species of subphylum 2 of Phylum III, and thereafter isolating the acid. Especially preferred for this purpose are species of the orders Mucorales, Hypocreales, Moniliales, and Actinomycetales. Also especially preferred for this purpose are species of the families Mucoraceae, Cunninghamellaceae, Nectreaceae, Moniliaceae, Dematiaceae, Tuberculariaceae, Actinomycetaceae, and streptomycetaceae. Also especially preferred for this purpose are species of the genera Absidia, Circinella, Gongronella, Rhizopus, Cunninghamella, Calonectria, Aspergillus, Penicillium, Sporotrichum, Cladosporium, Fasrium, Norcardia, and Streptomyces. Examples of microorganisms falling within the scope of those preferred orders, families, and genera are listed in U.S. Pat. No. 3,290,226.

CHART G

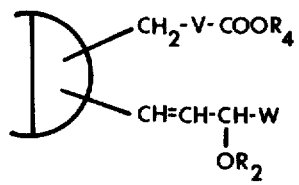

XLIII

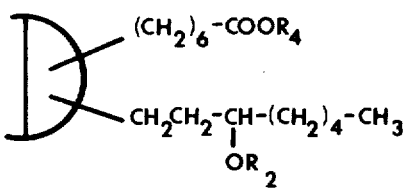

XLIV

This enzymatic ester hydrolysis is carried out by shaking the PGE-type 15-alkyl ether alkyl ester in aqueous suspension with the enzyme contained in a culture of one of the above-mentioned microorganism species until the ester is hydrolyzed. A reaction temperature in the range 20° to 30° C. is usually satisfactory. A reaction time of 1 to 20 hours is usually sufficient to obtain the desired hydrolysis. Exclusion of air from the reaction mixture, for example, with argon or nitrogen is usually desirable.

The enzyme is obtained by harvest of cells from the culture, followed by washing and resuspension of the cells in water, and cell disintegration, for example, by stirring with glass beads or by sonic or ultrasonic vibrations. The entire aqueous disintergration mixture is used as a source of the enzyme. Alternatively and preferably, however, the cellular debris is removed by centrifugation or filtration, and the aqueous supernatant or filtrate is used.

In some cases, it is advantageous to grow the microorganism culture in the presence of an alkyl ester of an aliphatic acid, said acid containing 10 to 20 carbon atoms, inclusive, and said alkyl containing 1 to 8 carbon atoms, inclusive, or to add such an ester to the culture and maintain the culture without additional growth for 1 to 24 hours before cell harvest. Thereby, the enzyme produced is sometimes made more effective in transforming the Formula-IV ester to the free acid. An example of a useful alkyl ester for this purpose is methyl oleate.

This enzymatic hydrolysis is also applicable to the alkyl esters of the PGF-type, PGA-type, and PGB-type 15-alkyl ethers.

When a PG-type 15-alkyl ether acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, for example, gives the ethyl, butyl, and 2-ethylhexyl esters, respectively.

Esterification with diazohyrocarbons is carried out by mixing a solution of the diazohydrocarbon in a suitable inert solvent, preferably ethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley & Sons, Inc., New York, N.Y., Vol. 8, pp. 389–394 (1954).

The final Formula II-through-XVII 15-alkyl ether PG-type compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the PG-type 15-alkyl ether acid in water containing the stoichiometric amount of a hydroxide, carbonate, or bicarbonate corresponding to the inorganic salt desired. For example, such use of sodium hyroxide, sodium carbonate, or sodium bicarbonate gives a solution of the sodium salts. Evaporation of the water or addition of a water-miscible solvent of moderate polarity, for example, a lower alkanol or a lower alkanone, gives the solid inorganic salt if that form is desired.

To produce an amine salt, the PG-type acid is dissolved in a suitable solvent of either moderate or low polarity. Examples of the former are ethanol, acetone, and ethyl acetate. Examples of the latter are ethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the PG-type acid with the stoichiometric amount of the corresponding quaternary ammonium hydroxide in water solution, followed by evaporation of the water.

DESCRIPTION OF THE PREFERRED EMBODIMENTS

The invention can be more fully understood by the following examples and preparations:

All temperatures are in degrees centigrade.

Infrared absorption spectra are recorded on a Perkin-Elmer model 421 infrared spectrophotometer. Except when specified otherwise, undiluted (neat) samples are used.

NMR spectra are recorded on a varian A-60 spectrophotometer on deuterochloroform solutions with tetramethylsilane as an internal standard (downfield).

Mass spectra are recorded on an Atlas CH-4 mass spectrometer with a TO-4source (ionization voltage 70 ev).

Ultraviolet spectra are recorded on a Cary Model 15 spectrophotometer.

The solvent systems used in thin layer chromatography herein include:

A. IX Ethyl acetate-acetic acid-2,2,4-trimethylpentane-water (90:20:50:100).

See M. Hamberg and B. Samuelsson, J. Biol. Chem. 241, 257 (1966).

"Brine" as used herein refers to a saturated aqueous solution of sodium chloride.

PREPARATION 1

3α-Benzoyloxy-5α-hydroxy-4-iodo-2β-methoxymethylcyclopentaneacetic Acid γ-Lactone (Formula XIX: $R_3$ is benzoyl).

Refer to Chart A. To a mixture of optically active laevorotatory (−) iodolactone XVIII (E. J. Corey et al., J. Am. Chem. Soc. Vol. 92, p. 397 (1970), 75 g.) in 135 ml. of dry pyridine under a nitrogen atmosphere is added 30.4 ml. of benzoyl chloride with cooling to maintain the temperature at about 20°–40° C. Stirring is continued for an additional 30 min. About 250 ml. of toluene is added and the mixture concentrated under reduced pressure. The residue is dissolved in one l. of ethyl acetate, washed with 10% sulfuric acid, brine, aqueous saturated sodium bicarbonate, and brine. The ethyl acetate solution is dried over sodium sulfate and concentrated under reduced pressure to yield an oil, 95 g. Crystallization of the oil yields the title compound, m.p. 84°–86° C.; $[\alpha]_D$ + 7° (CHCl$_3$); infrared spectral absorptions at 1768, 1722, 1600, 1570, 1490, 1275, 1265, 1180, 1125, 1090, 1060, 1030, and 710 cm$^{-1}$; and NMR (nuclear magnetic resonance) peaks at 2.1–3.45, 3.3, 3.58 4.38, 5.12, 5.51, 7.18–7.58, and 7.83–8.05 γ

Following the procedures of Preparation 1, the optically active Formula-XVIII iodolactone is transformed to a Formula-XIX compound using acetyl chloride instead of benzoyl chloride, to yield the corresponding intermediate wherein $R_3$ is acetyl.

Following the procedures of Preparation 1, but relacing that optically active Formula-XVIII iodolactone with the racemic compound of that formula and the mirror image thereof, and employing either benzoyl chloride or acetyl chloride, there is obtained the corresponding racemic Formula-XIX compound.

PREPARATION 2

3α-Benzoyloxy-5α-hydroxy-2β-methoxymethylcyclopentaneacetic Acid γ-Lactone (Formula XX: $R_3$ is benzoyl).

Refer to Chart A. To a solution of the optically active Formula-XIX benzoxy compound (Preparation 1, 60 g.) in 240 ml. of dry benzene is added 2,2'-azobis-(2-methylpropionitrile) (approximately 60 mg.). The mixture is cooled to 15° C. and to it is added a solution of 75 g. tributyltin hydride in 600 ml. of ether, with stirring, at such a rate as to maintain continuous reaction at about 25° C. When the reaction is complete as shown by TLC (thin layer chromatography) the mixture is concentrated under reduced pressure to an oil. The oil is mixed with 600 ml. of Skellysolve B (isomeric hexanes) and 600 ml. of water and stirred for 30 min. The water layer, containing the product, is separated, then combined with 450 ml. of ethyl acetate and enough solid sodium chloride to saturate the aqueous phase. The ethyl acetate layer, now containing the product, is separated, dried over magnesium sulfate, and concentrated under reduced pressure to an oil, 39 g. of the title compound. An analytical sample gives $[\alpha]_D$ −99° (CHCl$_3$); infrared spectral absorptions at 1775, 1715, 1600, 1585, 1490, 1315, 1275, 1180, 1110, 1070, 1055, 1025, and 715 cm$^{-1}$.; NMR peaks at 2.15–3.0, 3.25, 3.34, 4.84–5.17, 5.17–5.4, 7.1–7.5, and 7.8–8.05 γ; and mass spectral peaks at 290, 168, 105, and 77.

Following the procedures of Preparation 2, each of the optically active Formula-XIX compounds or their racemic compounds following Preparation 1 is transformed to the corresponding optically active Formula-XIX compound or its racemic compound.

PREPARATION 3

3α-Benzoyloxy-5α-hydroxy-2β-hydroxy-methylcyclopentaneacetic Acid γ-Lactone (Formula XXI: $R_3$ is benzoyl).

Refer to Chart A. To a cold (0°–5° C.) solution of lactone XX (Preparation 2, 20 g.) in 320 ml. of dichloromethane under nitrogen is added a solution of 24.8 ml. of boron tribromide in 320 ml. of dichloromethane, dropwise with vigorous stirring over a period of 50 min. at 0°–5° C. Stirring and cooling are continued for 1 hr. When the reaction is complete, as shown by TLC, there is cautiously added a solution of sodium carbonate (78 g. monohydrate) in 200 ml. of water. The mixture is stirred at 0°–5° C. for 10–15 min., saturated with sodium chloride, and the dichloro methane layer separated. Additional ethyl acetate extractions of the water layer are combined with the dichloro methane solution. The combined solutions are rinsed with brine, dried over sodium sulfate and concentrated under reduced pressure to an oil, 18.1 g. of the title compound. An analytical sample has m.p. 116–118° C.; $[\alpha]_D$ −80° (CHCl$_3$); infrared spectral absorptions at 3460, 1735, 1708, 1600, 1580, 1490, 1325, 1315, 1280, 1205, 1115, 1090, 1070, 1035, 1025, 730, and 720; and NMR peaks at 2.1–3.0, 3.58, 4.83–5.12, 5.2–5.45, 7.15–7.55, and 7.8–8.0 γ.

Following the procedures of Preparation 3, each of the optically active Formula-XX compounds or their racemic compounds following Preparation 2 is transformed to the corresponding optically active Formula-XXI hydroxymethyl compound or its racemate.

PREPARATION 4

3α-Benzoyloxy-2β-carboxaldehyde-5α-hydroxycyclopentaneacetic Acid γ-Lactone (Formula XXII: $R_3$ is benzoyl). Refer to Chart A. To a mixture of 150 ml. of dry dichloromethane and Collins' reagent (J. C. Collins et al., Tetrahedron Lett. 3363 (1968), 28 g.) at about 10° C. under nitrogen is added, with vigorous stirring, a cold (10° C.) solution of the optically active hydroxymethyl lactone XXI (Preparation 3, 5.0 g.) in 150 ml. of dichloromethane. After 5-min. additional stirring, about 100 ml. of dry benzene is added, the mixture is filtered, and the solution is concentrated under reduced pressure. The volume is brought to about 150 ml. with benzene. The solution of the Formula-XXII title compound is used directly.

From a similar run, there is obtained by concentration of the benzene solution under reduced pressure an oil which, on trituration with ether, yields crystals of the optically active Formula-XXII compound, m.p. 115° C. (dec.); and having NMR peaks at 1.8–3.7, 4.9–5.2, 5.54–5.77, 7.2–7.6, 7.7–8.0, and 9.8 γ.

Following the procedures of Preparation 4, each of the optically active Formula-XXI hydroxymethyl compounds or their racemic compounds following Preparation 3 is transformed to the corresponding optically active Formula-XXII aldehyde or its racemate wherein $R_3$ is either benzoyl or acetyl.

PREPARATION 5

3α-Benzoyloxy-5α-hydroxy-2β-oxo-trans-1-octenyl)-1α-cyclopentaneacetic Acid γ-Lactone (Formula XXIII: $R_3$ is benzoyl).

Refer to Chart A. A solution of dimethyl 2-oxo-heptylphosphonate (Corey et al, Journal of the American Chemical Society, 90, 3247 (1968)), in 36 ml. of THF is added, with stirring, to a cold (5° C.) suspension of sodium hydride (55%, 162 g.) in 180 ml. of THF. Thereafter the reaction mixture is stirred at about 25° C. for 2.5 hrs., and cooled to −10° C. To the mixture is added a benzene solution of optically active aldehyde XXII (Preparation 4, 108 ml.). After 1.5 hrs., 1.8 ml. of acetic acid is added and the THF distilled under vacuum. The residue is dissolved in ethyl acetate and the solution is washed with brine, dried over sodium sulfate, and concentrated under reduced pressure. Chromatography over silica gel using 25–30% ethyl acetate in Skellysolve B (isomeric hexanes) for elution yields the Formula-XXIII title compound.

Following the procedures of Preparation 5, but replacing the aldehyde XXII with each of the optically active Formula-XI aldehydes or their racemates disclosed following Preparation 4 there are obtained the corresponding Formula-XXIII compounds wherein $R_3$ corresponds to the $R_3$ moiety on the Formula-XXII aldehyde. The racemic Formula-XXII aldehydes each yield a corresponding Formula-XXIII racemate.

PREPARATION 6

3α-Benzoyloxy-5α-hydroxy-2β-(3α-hydroxy-trans-1-octenyl)-1α-cyclopentaneacetic Acid γ-Lactone (Formula XXIV: $R_3$ is benzoyl, and ~ is alpha).

Refer to Chart A. A solution containing ketone XXIII (Preparation 5, 2.75 g.) in 14 ml. of 1,2-dimethoxyethane is added to a mixture of zinc borohydride prepared from zinc chloride (anhydrous, 4.94 g.) in sodium borohydride (1.12 g.) in 48 ml. of dry 1,2-dimethoxyethane, with stirring and cooling to −10° C. Stirring is continued for 2 hrs. at 0° C., and water (7.8 ml.) is cautiously added, followed by 52 ml. of ethyl acetate. The mixture is filtered, and the filtrate is separated. The ethyl acetate solution is washed with brine, dried over sodium sulfate, and concentrated under reduced pressure to a mixture of the corresponding Formula-XXIV alpha and beta isomers. The compounds are subjected to chromatography on a silica gel column, eluting with ethyl acetate, to separate the alpha (less polar) and beta isomers of the Formula-XXIV title compounds.

Following the procedures of Preparation 6, the optically active Formula-XXIII ketones or their racemic mixtures described following Preparation 5, wherein $R_3$ is benzoyl or acetyl, are transformed to the corresponding optically active Formula-XXIV hydroxy compounds or their racemates.

EXAMPLE 1

3α-Benzoyloxy-5α-hydroxy-2β-(3α-methoxy-trans-1-octenyl)-1α-cyclopentaneacetic Acid γ-Lactone (Formula XXV: $R_2$ is methyl and $R_3$ is benzoyl).

Refer to Chart A where formulas for compounds XVIII through XXVI are shown. A mixture of the Formula-XXIV alpha hydroxy compound (Preparation 6, 2.0 g.), silver oxide (4.0 g.), and 50 ml. of methyl iodide is stirred and heated at reflux for 68 hrs. The mixture is cooled and filtered, and the filtrate concentrated to an oil, 2.0 g. Separation by silica gel chromatography, eluting with 35% ethyl acetate-Skellysolve B and combining those fractions shown by TLC to contain the product free of starting material and impurities, yields the Formula-XXV title compound as a yellow oil, 1.16 g. Infrared absorption at 1775, 1720, 1600, 1585, 1490, 1315, 1275, 1175, 1115, 1100, 1070, 1050, 1025, 970, and 715 cm$^{-1}$; NMR peaks at 0.8 (broad) 1.4 (broad), 1.9 (broad), 2.3 (broad), 2.7 (broad), 3.15 (singlet), 5.1 (broad), 5.4–5.6 (triplet), 7.5 (broad), and 7.8–8.0 (multiplet) γ.

Following the procedures of Example 1, but replacing the methyl iodide of that example with other alkyl halides, there are obtained the corresponding Formula-XXV alkyl ethers. Thus, with methyl bromide, ethyl chloride, isopropyl iodide, butyl bromide, or pentyl iodide, there are obtained the Formula-XXV compound in which $R_2$ is methyl, ethyl, isopropyl n-butyl or n-pentyl.

Following the procedures of Example 1 and using either methyl iodide or the alkyl halides in the paragraph above, each of the optically active or racemic Formula-XXIV hydroxy compounds following Preparation 6, wherein $R_3$ is benzoyl or acetyl, is transformed to the corresponding optically active Formula-XXV alkyl ether compound or racemate consisting of that compound and its mirror image.

EXAMPLE 1A

3α-Benzoyloxy-2β-(3α-tert-butoxy-trans-1-octenyl)-1α-cyclopentaneacetic Acid γ-Lactone (Formula XXV: $R_2$ is tert-butyl and $R_3$ is benzoyl).

Refer to Chart A. To a mixture of the Formula-XXIV alpha-hydroxy compound, viz. 3α-benzoyloxy-5α-hydroxy-2β-(3α-hydroxy-trans-1-octenyl)-1α-cyclopentaneacetic acid γ-lactone (Preparation 6, 2.0 g.) in 25 ml. of pyridine under nitrogen at 0° C., there is slowly added with stirring 4 ml. of methanesulfonyl chloride over a 15 min. period. Thereafter the mixture is stirred at 0° C. for 2.5 hrs., then cooled to −15° C. and mixed with 10 ml. of ice and water. After about 5 min., the mixture is poured into 250 ml. of ice and water. Cold 1:3 dichloromethaneether mixture (100 ml.) is added, followed by 150 ml. of cold 3N. hydrochloric acid. The organic layer is removed, washed with 2% sulfuric acid, water, aqueous sodium bicarbonate, and brine, then dried over sodium sulfate and concentrated under reduced pressure to the 3α-mesyloxy intermediate.

To a mixture of the above intermediate (2.2 g.) and pyridine (20 ml.) is added a mixture of potassium tert-butoxide (0.55 g.) and benzene (10 ml.) and the resulting mixture is stirred for several hours at about 25° C. under nitrogen. Thereafter the mixture is cautiously poured into 100 ml. of water and neutralized with cold 3 M. hydrochloric acid. The mixture is extracted with benzene and the benzene extracts are combined, washed with water and brine, dried over anhydrous sodium sulfate, and concentrated. The residue is separated by silica gel chromatography, eluting with 35% ethyl acetate-Skellysolve B and combining those fractions shown by TLC to contain the product free of starting material and impurities, to yield the Formula-XXV title compound.

Following the procedures of Example 1A, but replacing potassium tert-butoxide with sodium ethoxide, potassium isopropoxide, or sodium tert-pentyloxide, and using either the benzoyl or acetyl form of the Formula-XXIV compound, there is obtained the corresponding Formula-XXV compound wherein $R_2$ is ethyl, isopropyl, or tert-pentyl and $R_3$ is benzoyl or acetyl.

EXAMPLE 2

3α,5α-Dihydroxy-2β-(3α-methoxy-trans-1-octenyl)-1α-cyclopentaneacetic Acid γ-Lactone (Formula XXVI: $R_2$ is methyl).

Refer to Chart A. A mixture of the Formula-XXV benzoyloxy compound (1.91 g.) and anhydrous potassium carbonate (0.684 g.) in 25 ml. of dry methanol is stirred for 1 hr. with exclusion of moisture. Chloroform (25 ml.) is added and the mixture is filtered. The filtrate is concentrated to an oil which is taken up in chloroform (50 ml.). The solution is washed with brine, dried over magnesium sulfate, and concentrated to an oil. Separation by silica gel chromatography, eluting with 40% ethyl acetate-Skellysolve B and combining those fractions shown by TLC to contain the product free of starting material and impurities, yields the Formula-XXVI title compound as a pale yellow oil, 1.0 g.

Mass spectral peaks at 250, 211, 193, and 179; infrared spectral absorption at 3420, 1765, 1175, 1090, 1035, 975, and 905 cm$^{-1}$; NMR peaks at 0.8–1.1 (multiplet), 1.4 (broad), 1.9–2.4 (multiplet), 3.3 (singlet), 4.1 (multiplet), 5.1 (multiplet) and 5.5 (multiplet) 6. A sample is recrystallized from ether-Skellysolve B as needles, m.p. 57.5°–60° C.

Following the procedures of Example 2, each of the Formula-XXV alkyl ether compounds described following Example 1 and 1A is transformed to the corresponding optically active Formula-XXVI alkyl ether compound or racemate consisting of that compound and its mirror image. For example, the Formula-XXV compounds wherein $R_2$ is ethyl, isopropyl, butyl, tert-butyl, n-pentyl, or tert-pentyl yield the corresponding Formula-XXVI compounds wherein $R_2$ is ethyl, isopropyl, n-butyl, tert-butyl, n-pently, or tert-pentyl.

EXAMPLE 3

PGE$_2$, 15-Methyl Ether (Formula III: $R_1$ is hydrogen and $R_2$ is methyl).

Refer to Chart B, wherein steps (a) through (e) are shown, and formulas for compounds XXVI through XXXI, wherein $R_2$ is methyl.

a. The tetrahydropyranyl (THP) ether is prepared as follows. A mixture of the Formula-XXVI 3α,5α-dihydroxy-2β-(3α-methoxy-trans-1-octenyl)-1α-cyclopentaneacetic acid γ-lactone (2.35 g.), dihydropyran (3.5 g.), and p-toluene-sulfonic acid (about 0.01 g.) in 150 ml. of dichloromethane is stirred for 30 min. The mixture is washed twice with sodium carbonate (10%) solution, and brine, and dried over magnesium sulfate. Concentration under reduced pressure yields the Formula-XXVII THP ether, 32.6 g. free of starting material by TLC.

b. The Formula-XXVII lactol is prepared as follows. To a solution of the above THP ether in 150 ml. of dry toluene is added with stirring, protecting from air with nitrogen, a solution (105 ml.) of diisobutylaluminum hydride (10% in toluene) in about 35 min. at about –60° C. Stirring is continued for 30 min., with cooling. The cooling bath is removed, and a mixture of 48 ml. of tetrahydrofuran (THF) and 29 ml. of water is added dropwise over 20 min. The mixture is filtered, and the filtrate is washed with brine and dried over magnesium sulfate. Concentration under reduced pressure yields the Formula-XXVIII lactol as a yellow oil, 3.11 g., free of lactone by TLC.

c. The Formula-XXIX compound is obtained with a Wittig reagent prepared as follows. 4-Carboxybutyl triphenylphosphonium bromide (7.36 q.) obtained from Hal—(CH$_2$)$_4$—COOH wherein Hal is bromo or chloro by methods known in the art is added to a solution of sodio dimethylsulfinylcarbanide prepared from sodium hydride (57%, 1.4 g.) and 30 ml. or dimethylsulfoxide (DMSO), and the mixture is stirred for 20 min. at about 36° C. To this reagent is added dropwise the Formula-XXVIII lactol of step (b) (3.11 g.) in 25 ml. of DMSO. The mixture is stirred at about 25° C. for 3.5 hrs., then diluted with about 30 ml. of benzene. To it is added dropwise a solution of potassium hydrogen sulfate (5.96 g.) in 57 ml. of water with cooling and stirring. The mixture is diluted with 200 ml. of water and 100 ml. of benzene, separated, and the organic layer is washed with water and dried over magnesium sulfate. Concentration under reduced pressure yields an oil which is stirred with ether to further separate some solid by-products. Evaporation of the ether yields an oil which is separated by silica gel chromatography, eluting with 40% ethyl acetate-Skellysolve B, and combining those fractions shown by TLC to be free of starting material and impurities. Yield of Formula-XXIX compound, a yellow oil, 2.07 g.

d. The Formula-XXIX compound is oxidized to the Formula-XXX 9-oxo-compound as follows. To a solution of the 11-THP, 15-methyl ether compound of step (c) (0.887 g.) in 20 ml. of acetone at –20° C. is added dropwise 1.0 ml. of Jones reagent (2.1 g. of chromic anhydride, 6 ml. of water, and 1.7 ml. of concentrated sulfuric acid). After 15 min. stirring, 1 ml. of 2-propanol is added, with additional stirring. The mixture is poured into 100 ml. of water and extracted with dichloromethane. The organic extracts are washed with brine, dried over magnesium sulfate, and concentrated under reduced pressure to the Formula-XXX compound.

e. The Formula-XXX 11-THP compound is hydrolyzed to the Formula-XXXI PGE$_2$, 15-methyl ether, compound as follows. The product of step (d) is dissolved in a mixture of 20 ml. of acetic acid, 10 ml. of water, and 3 ml. of THF, and left standing at about 40° C. for 3 hrs. An additional 50 ml. of water is added, and the mixture is frozen and then freeze-dried under reduced pressure. Separation of the residual oil by silica gel chromatography, eluting with 40% ethyl acetate-Skellysolve B and combining those fractions shown by TLC to be free of starting material and impurities, yields the Formula-III, title compund is a tan oil, 0.4 g. Mass special peaks at 348, 334, 330, 316, 298, and 277: infrared spectral absorptions at 3420, 3300–3100, 2650, 1735, 1710, 1285, 1240, 1155, 1085, 1075, and 970 cm$^{-1}$; NMR peaks at 0.8–1.1 (multiplet), 1.4 (broad), 2.3 (broad), 3.3 (singlet), 3.4–3.6 (multiplet), 4.0–4.2 (multiplet), and 5.5 (broad) γ.

Following the procedures of Example 3, each of the optically active Formula-XXVI alkyl ethers or their racemic compounds following Example 2 is transformed to the corresponding Formula-XXIX intermediate and thence the Formula-XXXI PGE$_2$, 15-alkyl ether. For example, the optically active Formula-XXVI compound wherein $R_2$ is isopropyl yields PGE$_2$, 15-isopropyl ether; the racemate of the Formula-XXVI compound wherein $R_2$ is butyl yields racemic PGE$_2$, 15-butyl ether. In like manner, there are prepared other Formula-XXIX intermediates and Formula-III PGE$_2$-type products wherein $R_1$ is hydrogen, and $R_2$ is alkyl of one to 5 carbon atoms, inclusive, e.g. PGE$_2$, 15-ethyl ether, and PGE$_2$, 15-pentyl ether.

EXAMPLE 4

PGF$_2$ α , 15-Methyl Ether (Formula VII: $R_1$ is hydrogen, $R_2$ is methyl, and ~ is alpha).

Refer to Chart C, wherein $R_2$ is methyl. The Formula-XXIX THP-ether intermediate is hydrolyzed as follows. A mixture of the THP-ether (Example 3, step c, 2.07 g.), 40 ml. of acetic acid, 20 ml. of water, and 6 ml. of THF is maintained at about 38° C. for 4.5 hrs. An additional 100 ml. of water is added, and the mixture is frozen and then freeze-dried under reduced pressure. Separation of the residual oil-solids mixture by silica gel chromatography, eluting with 40% ethyl acetate-Skellysolve B and combining those fractions shown by TLC to be free of starting materials and impurities yields the Formula-VII title compound, 1.2 g. Crystallization from ether-Skellysolve B yields crystals, m.p. 52°–55° C. Mass spectral peaks at 353, 350, 336, 318, 300, 264, and 261; infrared spectral absorptions at 3420, 2950, 2720, 2660, 1715, 1680, 1330, 1270, 1205, 1130, 1075, 980, and 925 cm$^{-1}$; NMR peaks at 0.8–1.1 (multiplet), 1.5 (broad), 2.2 (broad), 3.3 (singlet) 4.0–4.3 (multiplet), and 5.5 (broad) γ.

Following the procedures of Example 4, but replacing that Formula-XXIX intermediate with those Formula-XXIX intermediates described following Example 3, there are obtained the corresponding optically active Formula-VII (XXXII) PGF$_2$$_\alpha$ alkyl ether products, for example PGF$_{2\alpha}$, 15-isopropyl ether; racemic PGF$_{2\alpha}$, 15-butyl ether; PGF$_{2\alpha}$, 15-methyl ether; and the like, wherein R$_2$ is within the scope as defined herein.

EXAMPLE 5

PGE$_1$, Methyl Ester, 15-Methyl Ether (Formula II: R$_1$ and R$_2$ are methyl).

Refer to Chart D, wherein D is

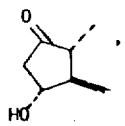

E is —CH=CH—, R$_2$ and R$_5$ are methyl, R$_4$ is hydrogen, V is —(CH$_2$)$_5$—, and W is 1-pentyl. A mixture of PGE$_1$ (0.25 g.), silver oxide (1.2 g.) and 50 ml. of methyl iodide is stirred and heated at reflux for 2 days. The mixture is cooled and filtered, and the filtrate concentrated. The residue is separated by silica gel chromatography, eluting with 10% acetone-dichloromethane. Those fractions shown by TLC to contain the 15-methyl ether compound free of starting materials and impurities are combined and concentrated to yield the Formula-II, (XXXIV) title compound. The PGE$_1$, methyl ester, 15-methyl ether has mass spectral peaks at 364, 332, 301, 300, and 293.

Following the procedure of Example 5, but replacing PGE$_1$ with PGE$_3$ or 13,14-dihydro-PGE$_1$, there are obtained the corresponding methyl ester, 15-methyl ether compounds of PGE$_3$ and 13,14-dihydro-PGE$_1$.

Likewise following the procedure of Example 5 but replacing PGE$_1$ with racemic PGE$_2$, racemic PGE$_3$, or racemic 13,14-dihydro-PGE$_1$, there are obtained the corresponding methyl ester, 15-methyl ether compounds of these racemic PGE compounds.

Likewise following the procedure of Example 5 but replacing the methyl iodide of Example 5 with other alkyl iodides, and employing either PGE$_1$, PGE$_2$, PGE$_3$, or 13,14-dihydro-PGE$_1$, there are obtained the corresponding Formula-XXXIV alkyl ester, 15-alkyl ether PGE-type compounds.

Likewise following the procedure of Example 5 but replacing PGE$_1$ with PGF$_1$$_\alpha$, PGF$_1$$_\beta$, PGF$_2$$_\alpha$, PGF$_2$$_\beta$, PGF$_3$$_\alpha$, PGF$_3$$_\beta$, 13,14-dihydro-PGF$_1$$_\alpha$, or 13,14-dihydro-PGF$_1$$_\beta$, or their racemates, there are obtained the corresponding methyl ester, 15-methyl ether PGF-type compounds within the scope of Formula XXXIV and their racemates.

EXAMPLE 5A

PGE$_2$, Methyl Ester, 15-Methyl Ether (Formula III; R$_1$ and R$_2$ are methyl).

Refer to Chart D, wherein D is

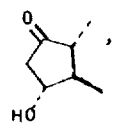

E is —CH=CH—, R$_2$ and R$_5$ are methyl, R$_4$ is hydrogen, V is —CH=CH—(CH$_2$)$_3$—, and W is 1-pentyl. A solution of PGE$_2$ (1.6 g.) in 150 ml. of dichloromethane is treated at about 25° C. with an ether solution of diazomethane containing 0.5 ml. of boron trifluoride etherate (see Fieser et al., "Reagents for Organic Synthesis," p. 192, John Wiley & Sons, Inc., New York, N.Y. (1967) until the bright yellow diazomethane color persists for 10 min.

Excess diazomethane is destroyed with a few drops of acetic acid and the solvent is removed under reduced pressure. The residue is separated into components by silica gel chromatography. Those fractions shown to contain the title compound free of the methyl ester of the starting compound and by-products by thin layer chromatography (TLC) are combined to yield the Formula-III (XXXIV, title compound.

Following the procedures of EXample 5A, but replacing the PGE$_2$ of that example with PGE$_1$, PGE$_3$, or 13,14-dihydro PGE$_1$, there are obtained the corresponding methyl ester, 15-methyl ether compounds of PGE$_1$, PGE$_3$, or 13,14-dihydro PGE$_1$.

Likewise following the procedures of Examples 5A, but replacing the diazomethane of that example with other diazoalkanes, there are obtained the corresponding Formula-XXXIV alkyl ester, 15-alkyl ether PGE-type products. Thus, with diazoethane, diazopropane, or diazobutane, and PGE$_1$ there are obtained the corresponding Formula-III (XXXIV) products: PGE$_1$, ethyl ester, 15-ethyl ether: PGE$_1$, propyl ester, 15-propyl ether; and PGE$_1$, butyl ester, 15-butyl ether. Starting with PGE$_1$, methyl ester, y PGE$_1$, methyl ester, 15-ethyl ether; PGE$_1$, methyl ester, 15-propyl ether; and PGE$_1$, methyl ester, 15-butyl ether.

EXAMPLE 5B

PGF$_2$ $\alpha$, Methyl Ester, 15-Methyl Ether (Formula VII: R$_1$ and R$_2$ are methyl and ~ is alpha).

Refer to Chart D wherein D is

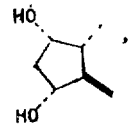

E is —CH=CH—, R$_2$, R$_4$, and R$_5$ are methyl, V is —CH=CH—(CH$_2$)$_3$—and W is 1-pentyl. A solution of PGF$_2$$_\alpha$, methyl ester (1.0 g.) in 20 ml. of methanol is treated with boron trifluoride etherate (0.25 ml.) at about 25° C. and left standing for 1 hr. Water (about 10 ml.) is added and the mixture is concentrated under vacuum to remove most of the methanol. The residue is extracted with ethyl acetate and the combined ethyl acetate extracts are washed with brine, dried over anhydrous magnesium sulfate, and concentrated under reduced pressure. The residue is taken up in a small amount of dichloromethane and separated by silica gel chromatography, to yield the Formula-XII (XXXIV) title compound.

Following the procedure of Example 5B, but replacing PGF$_2$ $_\alpha$, methyl ester, with the ethyl, propyl, isobutyl, and heptyl esters of PGF$_2$ $_\alpha$, there are obtained the corresponding ethyl, propyl, isobutyl, and heptyl esters of PGF$_{2\alpha}$, 15-methyl ether.

Likewise following the procedure of Example 5B, but replacing PGF$_{2\alpha}$, methyl ester, with racemic PGF$_{2\alpha}$, methyl ester, there is obtained racemic PGF$_2$ $_\alpha$, methyl ester, 15-methyl ester. Likewise the ethyl, propyl, isobutyl, and heptyl esters of racemic PGF$_2$ $_\alpha$ yield the corresponding esters of racemic PGF$_{2\alpha}$, 15-methyl ether.

Likewise following the procedure of Example 5B, but replacing the methanol of that example with other alcohols, e.g. ethanol, propanol, butanol, or pentanol, there are obtained the corresponding PGF$_{2\alpha}$ alkyl ester, 15-alkyl ether compounds wherein $R_2$ is ethyl, propyl, butyl or pentyl.

EXAMPLE 6

PGA$_2$, Methyl Ester, Methyl Ether (Formula XI: $R_1$ and $R_2$ are methyl),

Refer to Chart D wherein D is

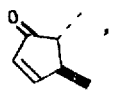

E is —CH=CH—, $R_2$ and $R_5$ are methyl, $R_4$ is hydrogen, V is —CH=CH—(CH$_2$)$_3$—, abd W is 1-pentyl. A mixture of PGA$_2$ (0.237 g.), silver oxide (0.41 g.), and 40 ml. of methyl iodide is stirred and heated at reflux for 17 hrs. The mixture is cooled and filtered, and the filtrate concentrated to a yellow oil. Separation by silica gel chromatography, eluting with 0.5-1.0% methanol-dichloromethane, yields the Formula-XI title compound, 0.04 g., as a yellow oil. Mass spectral peaks at 331, 330, 291, and 250; $\gamma_{max.}$, in ethanol, 217 ($\epsilon$=9,300) and 274 ($\epsilon$=1,550) m$\mu$.

Following the procedure of Example 6, PGA$_1$, PGA$_3$, and dihydro PGA, are converted to the corresponding Formula-XI compounds, for example PGA$_1$, methyl ester, methyl ether, and the like.

EXAMPLE 6A

PGA$_1$, 15-(tert-Butyl) Ether, Methyl Ester (Formula X: $R_1$ is methyl and $R_2$ is tert-butyl).

To a solution of PGA$_1$, methyl ester (5.0 g.) in 50 ml. of pyridine at 0° C. under nitrogen is added slowly with stirring 7 ml. of methanesulfonyl chloride over a period of 15 min. Thereafter the mixture is stirred at 0° C. for 2.5 hrs., then cooled to −15° C. and mixed with 10 ml. of ice and water. After about 5 min., the mixture is poured into 500 ml. of ice and water. Cold 1:3 dichloromethane ether mixture (200 ml.) is added, followed by 300 ml. of cold 3 M hydrochloric acid. The organic layer is removed, washed with 2% sulfuric acid, water, aqueous sodium bicarbonate, and brine, then dried over sodium sulfate and concentrated under reduced pressure to yield the 15-mesylate.

To a mixture of the 15-mesylate (4.13 g.) and pyridine (30 ml.) is added a mixture of potassium tert-butoxide (1.12 g.) and benzene (20 ml.) and the resulting mixture is stirred for several hours at about 25° C. under nitrogen. Thereafter the mixture is cautiously poured into 200 ml. of water and neutralized with cold 3 M hydrochloric acid. The mixture is extracted with benzene and the benzene extracts are combined, washed with water and brine, dried over anhydrous sodium sulfate, and concentrated. The residue is separated by silica gel chromatography, eluting with 50-100% ethyl acetate-Skellysolve B and combining those fractions shown by TLC to contain the desired 15α-(tert-butyl) ether, thereafter concentrating under reduced pressure to yield the Formula-X title compound.

EXAMPLE 7

PGB$_2$, Methyl Ester, Methyl Ether (Formula XV: $R_1$ and $R_2$ are methyl).

Refer to Chart D wherein D is

E is —CH=CH—, $R_2$ and $R_5$ are methyl, $R_4$ is hydrogen, V iis —CH=CH—(CH$_2$)$_3$—, and W is 1-pentyl. A solution of PGB$_2$ (1.63 g.) is stirred with silver oxide (5 g.), methyl iodide (20 ml.), and 200 ml. of benzene and heated at reflux under a water separator for 18 hrs. The mixture is filtered, and the filtrate concentrated to a yellow oil. Separation by silica gel chromatography, eluting with 2% acetone-dichloromethane, yields the Formula-XV title compound, 0.3 g., as a yellow-brown oil. Ultraviolet absorption: $\gamma_{max.}$, in ethanol, 277 ($\epsilon$=25,450) m$\mu$. Mass spectral peaks at 331, 330, and 291.

Following the procedure of Example 7, PGB$_1$, PGB$_3$, and dihydro-PGB$_1$ are converted to the corresponding Formula-XV compounds, for example, PGB$_1$, methyl ester, methyl ether, and the like.

EXAMPLE 8

PGF$_1$ $_\alpha$, Methyl Ester, 15-Methyl Ether (Formula VI: $R_1$ and $R_2$ are methyl and ~ is alpha) and PGF$_1$ Methyl Ester, 15-Methyl Ether (Formula VI: ~ is beta).

Refer to Chart E wherein E is —CH=CH—, $R_2$ and $R_4$ are methyl, V is —(CH$_2$)$_5$—, W is 1-pentyl, and ~ is either alpha or beta. A solution of sodium borohydride (0.6 g.) in 10 ml. of methanol at 0° C. is added to a solution of PGE$_1$, methyl ester, 15-methyl ether (Example 5, 1.5 g.) in 60 ml. of methanol and the mixture is stirred at 0° C. for 30 minutes. Acetone (10 ml.) is added and the solution is made slightly acid with dilute acetic acid in methanol. The mixture is concentrated by evaporation under reduced pressure and the residue is taken up in dichloromethane. The resulting solution is washed with brine, dried over sodium sulfate and evaporated under reduced pressure. The residue is chromatographed over silica gel wet-packed in 8% methanol in dichlormethane ad rinsed with 300 ml. of dichloromethane, eluting with 2–10% methanol-dichloromethane. Those fractions shown by TLC to contain PGF$_{1\alpha}$, methyl ester, 15-methyl ether free of starting material and impurities are combined and concentrated to yield the Formula -VI PGF$_{1\alpha}$ -type title compound. Likewise, those fractions shown by TLC to contain PGF$_{1\beta}$, methyl ester, 15-methyl ether are combined and concentrated to yield the Formula-VI PGF$_{1\beta}$ -type title compound.

Following the procedures of Example 8, each of the PGE$_1$, alkyl ester, 15-alkyl ether compounds of and following Examples 3, 5, and 5A is transformed to the corresponding PGF α and PGF β optically active and racemic compounds.

EXAMPLE 8A

PGF$_{2\alpha}$, Methyl Ester, 15-Methyl Ether (Formula VII: R$_1$ and R$_2$ are methyl, and ~ is alpha) and PGF$_2$ $_\beta$ Methyl Ester, 15-Methyl Ether (Formula VII: ~ is beta).

Refer to Chart F, wherein E is —CH=CH—, R$_2$, R$_4$, and R$_6$ are methyl, R$_7$ is (CH$_3$)$_3$Si—, V is —CH=λ CH—(CH$_2$)$_3$—, W is 1-pentyl, and ~ is alpha or beta. A solution of PGE$_2$, methyl ester, 15-methyl ether (Example 1, 1.0 g.) in 20 ml. of dry tetrahydrofuran (THF) is stirred with 3 ml. of hexamethyldisilazane and 0.6 ml. of trimethyl chlorosilane for 20 hrs. at about 25° C., with protection from moisture. The mixture is concentrated under reduced pressure, then taken up in 50 ml. of dry benzene and again concentrated. The residue is dissolved in 150 ml. of cold methanol and treated, with stirring, with a cold (−10° C) solution of sodium borohydride (2.8 g.) in 150 ml. of methanol, maintaining the temperature below about 10° C. After 10 minutes of additional stirring, there is added 5 ml. of acetone and sufficient acetic acid to neutralize the mixture. The mixture is concentrated under reduced pressure to about 75 ml. Water (about 75 ml.) is added to hydrolyze the trimethylsilyl group thereafter stirring at about 25° C. for 3 hrs. When the trimethylsilyl group is removed, as shown by TLC, the mixture is concentrated under reduced pressure to remove most of the methanol. The remaining solution is extracted with ethyl acetate, and the combined ethyl acetate extracts are washed with brine, dried over anhydrous magnesium sulfate, and concentrated under reduced pressure. The residue is taken up in a minimum amount of dichloromethane and subjected to silica gel chromatography, eluting with 50–100% ethylacetate-Skellysolve B (isomeric hexanes). Those fractions shown to contain the 9α-hydroxy title compound free of starting compound and by-products by TLC are combined to yield the PGF$_{2\alpha}$ -type Formula-VII title compound. Mass spectral peaks at 382, 364, 350, 346, and 332; infrared spectral absorptions at 3410, 1735, 1660, 1435, 1365, 1315, 1240, 1215, 1195, 1170, 1090, and 970 cm.$^{-1}$; NMR peaks at 5.42 (multiplet), 3.9 (multiplet), 3.64, 3.49, 3.21, and 0.9 (triplet) 6.

Likewise, those fractions shown by TLC to contain PGF$_{2\beta}$, methyl ester, 15-methyl ether are combined and concentrated to yield the Formula-VII PGF$_{2\beta}$ -type title compound.

Following the procedures of Example 8A, but replacing PGE$_2$, methyl ester, 15-methyl ether with PGE$_2$, 15-methyl ether (Example 3) there is obtained PGF$_{2\alpha}$, 15-methyl ether. Likewise, each of the esters of PGE$_2$, 15-methyl ether, described following Example 3 yields the corresponding ester of PGF$_{2\alpha}$, 15-methyl ether.

EXAMPLE 9

PGA$_1$, Methyl Ether (Formula X: R$_1$ is hydrogen and R$_2$ is methyl).

Refer to Chart E, wherein E is —CH=CH—, R$_2$ is methyl, R$_4$ is hydrogen, V is —(CH$_2$)$_5$—, and W is 1-pentyl. A mixture of PGE$_1$, 15-methyl ether, (0.4 g.), glacial acetic acid (9 ml.), and water (1 ml.) is heated under nitrogen at 60° C. for 18 hrs. The mixture is concentrated under reduced pressure, and the residue is subjected to silica gel chromatography, eluting with 25–100% ethyl acetate-Skellysolve B. The fractions shown by TLC to contain the desired product free of starting material and impurities are combined and concentrated to give the Formula-X PGA$_1$-type title compound.

Following the procedures of Example 9, each of the PGE-type compounds described following Examples 3, 5, and 5A is transformed to the corresponding PGA-type alkyl ether.

EXAMPLE 10

PGB$_1$, Methyl Ether (Formula XIV: R$_1$ is hydrogen and R$_2$ is methyl).

Refer to Chart E, wherein E is —CH=CH—, R$_2$ is methyl, R$_4$ is hydrogen, V is —(CH$_2$)$_5$—, and W is 1-pentyl. A mixture of PGE$_1$, 15-methyl ether (0.2 g.), potassium hydroxide (10 g.), and 100 ml. of 50% aqueous ethanol is maintained at about 25° C. for 10 hrs. under nitrogen. The mixture is then cooled to 10° C. and neutralized by addition of 3 N hydrochloric acid at 10° C. The resulting solution is extracted repeatedly with ethyl acetate, and the combined ethyl acetate extracts are washed with water and brine, dried, and concentrated to the formula XIV PGB$_1$-type title compound.

Following the procedures of Example 10, each of the PGE-type compounds described following Examples 3, 5, and 5A is transformed to the corresponding PGB-type alkyl ether.

EXAMPLE 11

13,14 -Dihydro-PGE$_1$, 15-Methyl Ether (Formula V: R$_1$ is hydrogen and R$_2$ is methyl).

Refer to Chart G wherein D is

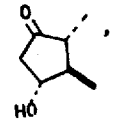

R$_2$ is methyl, R$_4$ is hydrogen, V is —(CH$_2$)$_5$—, and W is 1-pentyl. A solution of PGE$_1$, 15-methyl ether (100 mg.) in 10 ml. of ethyl acetate is shaken with hydrogen at about 1 atmosphere pressure at 25°C. in the presence of 5% palladium on charcoal (15 mg.). One equivalent of hydrogen is absorbed in about 90 minutes. The hydrogenation is then stopped, and the catalyst is removed by filtration. The filtrate is evaporated, and the residue is chromatographed on 25 g. of silica gel, eluting with a 50–100% ethyl acetate gradient in Skellysolve B. Those fractions shown by TLC to contain the desired product free of the starting produuct and dehydration products are combined and evaporated to give the Formula-V 13,14-dihydro-PGE₁-type title compound.

Following the procedure of Example 11, PGE₁, 15-methyl ether, ethyl ester is reduced to 13,14-dihydro-PGE₁, 15-methyl ether, ethyl ester.

Also following the procedure of Example 11, PGE₂, 15-methyl ether, and PGE₃, 15-methyl ether, are each reduced to 13,14-dihydro-PGE₁, 15-methyl ether using two equivalents of hydrogen for the first reaction and three equivalents of hydrogen for the second.

Also following the procedure of Example 11, the ethyl ester and the free acid form of the Formula II-to-IV PGE compounds, 15-alkyl ethers, transformed to the corresponding 13,14-dihydro PGE₁, 15alkyl ether compounds by catalytic hydrogenation, using equivalents of hydrogen appropriate to the degree of unsaturation of the reactant, i.e., one equivalent for the PGE₁-type, two equivalents for the PGE₂-type, and three equivalents for the PGE₃-type compounds.

Also following the procedure of Example 11, PGF₁α, 15-methyl ether, and its ethyl ester are reduced to 13,14-dihydro-PGF₁α, 15-methyl ester, and its ethyl ester, respectively.

Also following the procedure of Example 11, the ethyl ester and the free acid form of the Formula VI-to-VIII PGF 15-alkyl ester compounds are transformed to the corresponding 13,14-dihydro PGF₁α or PGF₁β 15-alkyl ester compounds by catalytic hydrogenation, using equivalents of hydrogen appropriate to the degree of unsaturation of the reactant.

EXAMPLE 12

13,14-Dihydro-PGA₁, Methyl Ether (Formula XIII: R₁ is hydrogen and R₂ is methyl).

Refer to Chart G wherein D is

R₂ is methyl, R₄ is hydrogen, v is —(CH₂)₅— and W is 1 pentyl. A suspension of disodium azodiformate (50 mg.) in 5 ml. of absolute ethanol is added to a stirred solution of PGA₁, methyl ether (50 mg.) in 10 ml. of absolute ethanol under nitrogen at 25°C. The mixture is made acid with glacial acetic acid, and then is stirred under nitrogen at 25°C. for 8 hours. The resulting mixture is evaporated under reduced pressure and the residue is mixed with a mixture of diethyl ether and water (1:1). The diethyl ether layer is separated, dried, and evaporated to give the Formula-XIII 13,14-dihydro PGA₁-type title compound.

Following the procedure of Example 12, PGA₁, methyl ester, methyl ether is reduced to 13,14-dihydro-PGA₁, methyl ester, methyl ether.

Also following the procedure of Example 12, PGA₂, methyl ether, and PGA₃, methyl ether, are each reduced to 13,14-dihydro-PGA₁, methyl ether using amounts of the disodium azodiformate rectant appropriate to the degree of unsaturation of the reactant.

Also following the procedure of Example 12, the methyl ester and the free acid form of the 15-alkyl ethers of the Formula II-to-IV PGE-type compounds, the formula VI-to-VIII PGF compounds, the Formula X-to-XII PGA compounds, and the Formula XIV-to-XVI PGB compounds are transformed to the corresponding 13,14-dihydro PGE₁-, PGF₁, PGA₁-, or PGB₁-type 15-alkyl ether compounds, by diimide reduction, using amounts of disodium azodiformate reactant appropriate to the degree of unsaturation of the PGE-, PGF-, PGA,- or PGB-type 15-alkyl ether reactant.

EXAMPLE 13

PGF₂α, 15-Methyl Ether (Formula VII: R₁ is hydrogen, R₂ is methyl, and ~ is alpha).

Refer to Chart D, step g, wherein D is

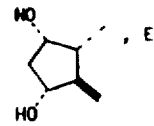

is 13 CH=CH—, R₂ and R₄ are methyl, V is —CH=CH—(CH₂)₃—, and W is 1-pentyl. A solution of PGF₂α, methyl ester, 15-methyl ether (Example 5B, 0.15 g.) in a mixture of methanol (4.5 ml.) and water (1.5 ml.) is cooled to 5°C. and 0.6 ml. of 45% aqueous potassium hydroxide is added. The mixture is left standing 3.5 hrs. at about 25°C., then is diluted with 75 ml. of water and extracted with ethyl acetate to remove any neutral material. The aqueous layer is acidified with dilute hydrochloric acid and extracted several times with ethyl acetate. The combined ethyl acetate extracts are washed with water and brine, dried over sodium sulfate, and evaporated to give the Formula-VII title compound. Mass spectral peaks at 353, 350, 336, 318, 300, 264, and 261; infrared spectral absorptions at 3420, 2950, 2720, 2660, 1715, 1680, 1330, 1270, 1205, 1130, 1075, 980, and 925 cm⁻¹.

Following the procedure of Example 13, each of the esters of PGF₂α, 15-methyl ether, described following Example 5B, as well as each of the esters of racemic PGF₂α, 15-methyl ether, is saponified to yield the corresponding PGF₂α, 15-methyl ether, or racemic PGF₂α, 15-methyl ether free acid. Likewise the esters of PGF₂β, 15-methyl ether, and racemic PGF₂β, 15-methyl ether, are saponified to the corresponding free acids.

EXAMPLE 14

PGE₂, 15-Methyl Ether (Formula III: R₁ is hydrogen, and R₂ is methyl).

A solution of PGF₂α, 15-methyl ether, (0.1 g.) in 40 ml. of acetone is cooled to —10°C. To it is added 110% of the theoretical amount of Jones reagent (in the proportions of 21 g. of chromic anhydride, 60 ml. of water, and 17 ml. of concentrated sulfuric acid), precooled by 0°C., with vigorous stirring. After about 10 min., isopropyl alcohol (1 ml.) is added to the cold reaction mixture. After 5 min., the mixture is filtered and the filtrate is concentrated under reduced pressure. The residue is mixed with 5 ml. of brine and the mixture is extracted several times with ethyl acetate. The combined ethyl acetate extracts are washed with brine, dried with anhydrous sodium sulfate, and concentrated under reduced pressure. The residue is subjected to silica gel chromatography, eluting with 50–100% ethyl acetate-Skellysolve B. Those fractions shown by TLC to contain the desired product are combined and concentrated to Formula-II the Formula title compound. Mass spectral peaks at 348, 334, 330, 316, 298, and 277; infrared spectral absorptions at 3420, 3200 (broad), 2650, 1735, 1710, 1285, 1240, 1155, 1085, 1075, and 970 cm$^{-1}$.

Following the procedure of Example 14 but replacing PGF$_{2\alpha}$, 15-methyl ether, with racemic PGF$_{2\alpha}$, 15-methyl ether, there is obtained racemic PGE$_2$, 15-methyl ether.

EXAMPLE 15

PGE$_1$, 15-Methyl Ether Free Acid by Enzymatic hydrolysis (Formula II: R$_1$ is hydrogen, and R$_2$ is methyl).

A. Enzyme preparation

A medium is prepared consisting of 2% corn steep liquor (a mixture of equal parts of cerelose and glucose) in tap water. This is brought to pH 4.5 by adding hydrochloric acid, and 1% of methyl oleate is added. Four 500 ml. flasks each containing 100 ml. of the above medium are inoculated with Cladosporium resinae (C1-11, AICC 11,274; and are placed on a shaker at room temperature (about 28°C.) for 4 days. The culture is then placed in 40 ml. centrifuge tubes and centrifuged at about 2000 rmp. in a clinical centrifuge. The liquid is decanted from the centrifuge tubes and the collected cells are washed with cold water. The washed cells from 2 centrifuge tubes are suspended in 50 ml. of ice cold 0.05 M pH 7.0 phosphate buffer and placed in small Waring blender cup chilled with ice. Glass beads are added and the suspended cells are churned in the blender for 15 minutes. The resulting suspension of broken cells is centrifuged in a clinical centrifuge at about 2000 r.p.m. for 15 minutes at room temperature, then the supernatant liquid is collected. This supernatant liquid contains Cladosporium resinae acylase and is used directly for the hydrolysis of alkyl esters or is stored, preferably frozen, until needed.

B. Esterase hydrolysis

Ten milliliters of the supernatant liquid containing Cladosporium resinae acylase, prepared as described in part A of this example and 50 mg. of PGE$_1$, 15-methyl ether, methyl ester are shaken at room temperature under nitrogen for about 19 hours, then 70 ml. of acetone is added and the mixture is filtered giving a filtrate and an insoluble residue. The filtrate is evaporated under reduced pressure. The residue is subjected to silica gel chromatography, eluting with 50–100% ethyl acetate-Skellysolve B, combining those fractions shown by TLC to contain the product free of starting material and impurities, and concentrating to the Formula-II free acid product.

Following the procedure of Example 15, each of the methyl, ethyl, and other alkyl esters defined above in and after Examples 3, 5, 5A, 5B, 6, 6A, 7, 8, 8A, 9, 10, 11, and 12 is hydrolyzed enzymatically to the corresponding 15-alkyl ether PG-type free acid.

EXAMPLE 16

PGA$_1$, Methyl Ether, Methyl Ester (Formula XIII: R$_1$ and R$_2$ are methyl).

A solution of diazomethane (about 50% excess) in diethyl ether (25 ml.) is added to a solution of 15-methyl-PGA$_1$, (Example 9, 50 mg.) in 25 ml. of a mixture of methanol and ethyl ether (1:1). The mixture is allowed to stand at 25°C. for 5 min. Then, the mixture is evaporated to give the Formula-XIII title compound.

Following the procedure of Example 16, each of the other specific 15-alkyl ether PGE-type, PGF-type, PGA-type, and PGB-type free acids defined above is converted to the corresponding methyl ester.

Also following the procedure of Example 16, but using in place of the diazomethane, diazoethane, diazobutane, 1-diazo-2-ethylhexane, and diazocyclohexane, there are obtained the corresponding ethyl, butyl, 2-ethylhexyl, and cyclohexyl esters of PGA$_1$, methyl ether. In the same manner, each of the other specific 15-alkyl ether PGE-type, PGF-type, PGA-type, and PGB-type free acids defined above is converted to the corresponding ethyl, butyl, 2-ethylhexyl, and cyclohexyl esters.

EXAMPLE 17

PGE$_2$, 15-Methyl Ether, Sodium Salt (FOrmula III: R$_1$ is sodium and R$_2$ is methyl).

A solution of PGE$_2$, 15-methyl ether (Example 3, 100 mg.) in 50 ml. of water-ethanol mixture (1:1) is cooled to 5°C. and neutralized with an equivalent amount of 0.1 N aqeuous sodium hydroxide solution. The neutral solution is evaporated to give the title compound.

Following the procedure of Example 17 but using potassium hydroxide, calcium hydroxide, tetramethylammonium hydroxide, and benzyltrimethylammonium hydroxide in place of sodium hydrodixe, there are obtained the corresponding salts of PGE$_2$, 15-methyl ether.

Also following the procedure of Example 17 each of the 15-alkyl ether PGE$_2$-type, PGF$_2$-type, PGA$_2$-type, and PGB$_2$-type acids defined above is transformed to the sodium, potassium, calcium, tetramethylammonium, and benzyltrimethylammonium salts.

We claim:

1. An optically active compound of the formula

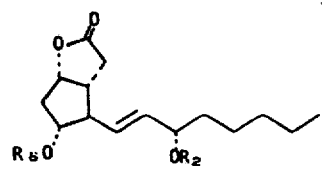

or a racemic compound of that formula and the mirror image thereof, wherein R$_2$ is alkyl of 1 to 5 carbon atoms, inclusive, and R$_8$ is hydrogen, tetrahydropyranyl, benzoyl, or acetyl.

2. An optically active or racemic compound according to claim 1 wherein R$_8$ is hydrogen.

3. An optically active or racemic compound according to claim 1 wherein R$_2$ is methyl and R$_8$ is hydrogen.

4. A compound according to claim 1 wherein R$_8$ is tetrahydropyranyl.

5. A compound according to claim 4 wherein R$_2$ is methyl.

6. A compound according to claim 1 wherein R$_8$ is benzoyl.

7. A compound according to claim 6 wherein R$_2$ is methyl.

8. A compound according to claim 1 wherein R$_8$ is acetyl.

9. A compound according to claim 8 wherein R$_2$ is methyl.

* * * * *